United States Patent
Grabarnick et al.

(10) Patent No.: US 11,632,954 B2
(45) Date of Patent: Apr. 25, 2023

(54) POLYMORPHS OF 5-FLUORO-4-IMINO-3-METHYL-1-TOSYL-3,4-DIHYDROPYRIMIDIN-2-ONE

(71) Applicant: ADAMA MAKHTESHIM LTD., Beer Sheva (IL)

(72) Inventors: Michael Grabarnick, Meitar (IL); Gal Suez, Beer Sheva (IL); Zoltán Német, Liestal (CH); Samaa Alasibi, Hura (IL)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 0 days.

(21) Appl. No.: 16/632,068

(22) PCT Filed: Jul. 16, 2018

(86) PCT No.: PCT/IB2018/000875
§ 371 (c)(1),
(2) Date: Jan. 17, 2020

(87) PCT Pub. No.: WO2019/038583
PCT Pub. Date: Feb. 28, 2019

(65) Prior Publication Data
US 2020/0229437 A1  Jul. 23, 2020

Related U.S. Application Data

(60) Provisional application No. 62/533,509, filed on Jul. 17, 2017.

(51) Int. Cl.
*A01N 43/54* (2006.01)
*C07D 239/47* (2006.01)

(52) U.S. Cl.
CPC .......... *A01N 43/54* (2013.01); *C07D 239/47* (2013.01); *C07B 2200/13* (2013.01)

(58) Field of Classification Search
CPC .... C07D 239/47; C07B 2200/13; A01N 43/54
(Continued)

(56) References Cited

U.S. PATENT DOCUMENTS

| 3,309,359 A | 3/1967 | Duschinsky et al. |
| 3,368,938 A | 2/1968 | Berger et al. |

(Continued)

FOREIGN PATENT DOCUMENTS

| WO | WO 2008/093325 A2 | 8/2008 |
| WO | WO 2016/106138 A1 | 6/2016 |

OTHER PUBLICATIONS

Laurence Harwood et al., "Experimental organic chemistry—Principles and practice", Experimental Chemistry—Organic Chemistry and Reaction, Jan. 1, 1989, pp. 127-132.

Mino R. Caira, "Crystalline Polymorphism of Organic Compounds", Topics in Current Chemistry, Springer, Berlin, DE, vol. 198, Jan. 1, 1998, pp. 163-208.

(Continued)

*Primary Examiner* — Taylor V Oh
(74) *Attorney, Agent, or Firm* — Gary J. Gershik

(57) ABSTRACT

The present subject matter provides a crystalline form of the compound having the following structure:

(Continued)

wherein the crystalline form is a polymorph, hydrate or solvate.

39 Claims, 16 Drawing Sheets

(58) Field of Classification Search
USPC .......................................................... 514/274
See application file for complete search history.

(56) References Cited

U.S. PATENT DOCUMENTS

| | | | |
|---|---|---|---|
| 3,635,977 | A | 1/1972 | Lutz et al. |
| 3,868,373 | A | 2/1975 | Hoffer |
| 4,009,272 | A | 2/1977 | Konig et al. |
| 4,845,081 | A | 7/1989 | Sloan |
| 4,996,208 | A | 2/1991 | Lindner et al. |
| 5,962,489 | A | 10/1999 | Mueller et al. |
| 6,066,638 | A | 5/2000 | Bereznak et al. |
| 6,617,330 | B2 | 9/2003 | Walter |
| 7,914,799 | B2 | 3/2011 | Jira et al. |
| 8,263,603 | B2 | 9/2012 | Boebel et al. |
| 8,318,758 | B2 | 11/2012 | Boebel et al. |
| 8,470,839 | B2 | 6/2013 | Boebel et al. |
| 8,552,020 | B2 | 10/2013 | Pobanz et al. |
| 8,658,660 | B2 | 2/2014 | Boebel et al. |
| 8,916,579 | B2 | 12/2014 | Boebel et al. |
| 9,000,002 | B2 | 4/2015 | Pobanz et al. |
| 9,006,259 | B2 | 4/2015 | Webster et al. |
| 9,174,970 | B2 | 11/2015 | Benko et al. |
| 9,204,653 | B2 | 12/2015 | Boebel et al. |
| 9,271,497 | B2 | 3/2016 | Lorsbach et al. |
| 9,321,734 | B2 | 4/2016 | Lorsbach et al. |
| 9,526,245 | B2 | 12/2016 | Owen et al. |
| 9,532,570 | B2 | 1/2017 | Owen et al. |
| 9,538,753 | B2 | 1/2017 | Owen et al. |
| 9,642,368 | B2 | 5/2017 | Lorsbach et al. |
| 9,840,475 | B2 | 12/2017 | Lorsbach et al. |
| 9,840,476 | B2 | 12/2017 | Choy et al. |
| 9,850,215 | B2 | 12/2017 | Choy et al. |
| 9,862,686 | B2 | 1/2018 | Boebel et al. |
| 10,045,533 | B2 | 8/2018 | Owen et al. |
| 10,045,534 | B2 | 8/2018 | Owen et al. |
| 10,051,862 | B2 | 8/2018 | Owen et al. |
| 10,059,703 | B2 | 8/2018 | Lorsbach et al. |
| 10,426,165 | B2 | 10/2019 | Owen et al. |
| 10,426,166 | B2 | 10/2019 | Owen et al. |
| 10,426,167 | B2 | 10/2019 | Owen et al. |
| 2003/0039667 | A1 | 2/2003 | Jira et al. |
| 2003/0040521 | A1 | 2/2003 | Walter |
| 2007/0027034 | A1 | 2/2007 | Tank et al. |
| 2007/0249548 | A1 | 10/2007 | Kitade et al. |
| 2008/0004253 | A1 | 1/2008 | Branstetter et al. |
| 2008/0182847 | A1 | 7/2008 | Augeri et al. |
| 2008/0234295 | A1 | 9/2008 | Beck et al. |
| 2008/0269238 | A1 | 10/2008 | Sugihara et al. |
| 2008/0280917 | A1 | 11/2008 | Albrecht et al. |
| 2009/0203647 | A1 | 8/2009 | Benko et al. |
| 2010/0022538 | A1 | 1/2010 | Boebel et al. |
| 2010/0029482 | A1 | 2/2010 | Benko et al. |
| 2010/0029483 | A1 | 2/2010 | Iskandar et al. |
| 2010/0284959 | A1 | 11/2010 | Rayan et al. |
| 2011/0034490 | A1 | 2/2011 | Boebel et al. |
| 2011/0034491 | A1 | 2/2011 | Boebel et al. |
| 2011/0034492 | A1 | 2/2011 | Boebel et al. |
| 2011/0034493 | A1 | 2/2011 | Boebel et al. |
| 2011/0053891 | A1 | 3/2011 | Boebel et al. |
| 2011/0082162 | A1 | 4/2011 | Lorsbach et al. |
| 2011/0263627 | A1 | 10/2011 | Boebel et al. |
| 2012/0088665 | A1 | 4/2012 | Dietz et al. |
| 2012/0208700 | A1 | 8/2012 | Hopkins et al. |
| 2013/0045984 | A1 | 2/2013 | Boebel et al. |
| 2014/0011824 | A1 | 1/2014 | Boebel et al. |
| 2014/0024616 | A1 | 1/2014 | Boebel et al. |
| 2015/0111851 | A1 | 4/2015 | Boebel et al. |
| 2015/0181874 | A1 | 7/2015 | Owen et al. |
| 2015/0181875 | A1 | 7/2015 | Owen et al. |
| 2015/0181883 | A1 | 7/2015 | Owen et al. |
| 2015/0183749 | A1* | 7/2015 | Choy .................. C07D 239/47 544/317 |
| 2015/0183750 | A1 | 7/2015 | Choy et al. |
| 2015/0191436 | A1 | 7/2015 | Webster et al. |
| 2015/0342188 | A1 | 12/2015 | Lorsbach et al. |
| 2015/0353506 | A1 | 12/2015 | Lorsbach et al. |
| 2015/0359225 | A1 | 12/2015 | Lorsbach et al. |
| 2016/0198711 | A1 | 7/2016 | Lorsbach et al. |
| 2016/0280662 | A1 | 9/2016 | Choy et al. |
| 2016/0280663 | A1 | 9/2016 | Choy et al. |
| 2017/0008855 | A1 | 1/2017 | Boebel et al. |
| 2017/0086458 | A1 | 3/2017 | Owen et al. |
| 2017/0086459 | A1 | 3/2017 | Owen et al. |
| 2017/0086460 | A1 | 3/2017 | Owen et al. |
| 2017/0240540 | A1 | 8/2017 | Lorsbach et al. |
| 2018/0000082 | A1 | 1/2018 | Klittich et al. |
| 2018/0072686 | A1 | 3/2018 | Choy et al. |
| 2018/0303094 | A1 | 10/2018 | Owen et al. |
| 2018/0303095 | A1 | 10/2018 | Owen et al. |
| 2018/0303096 | A1 | 10/2018 | Owen et al. |
| 2019/0308941 | A1 | 10/2019 | Choy et al. |
| 2019/0373891 | A1 | 12/2019 | Owen et al. |
| 2019/0380342 | A1 | 12/2019 | Owen et al. |
| 2019/0380343 | A1 | 12/2019 | Owen et al. |
| 2020/0024238 | A1 | 1/2020 | Choy et al. |
| 2020/0100500 | A1 | 4/2020 | Owen et al. |
| 2020/0113182 | A1 | 4/2020 | Owen et al. |
| 2020/0113183 | A1 | 4/2020 | Owen et al. |
| 2020/0148649 | A1 | 5/2020 | Choy et al. |
| 2020/0221698 | A1 | 7/2020 | Owen et al. |
| 2020/0229438 | A1 | 7/2020 | Owen et al. |
| 2020/0245623 | A1 | 8/2020 | Owen et al. |
| 2020/0337309 | A1 | 10/2020 | Owen et al. |
| 2020/0359625 | A1 | 11/2020 | Owen et al. |
| 2020/0375180 | A1 | 12/2020 | Owen et al. |
| 2021/0037822 | A1 | 2/2021 | Owen et al. |
| 2021/0059252 | A1 | 3/2021 | Owen et al. |
| 2021/0059253 | A1 | 3/2021 | Owen et al. |

OTHER PUBLICATIONS

International Search Report dated Oct. 23, 2018 in connection with PCT International Application No. PCT/IB2018/000875.
Written Opinion (form PCT/ISA/237) dated Oct. 23, 2018 in connection with PCT International Application No. PCT/IB2018/000875.
U.S. Appl. No. 61/232,177, filed Aug. 7, 2009, Boebel.
U.S. Appl. No. 61/232,204, filed Aug. 7, 2009, Webster.
U.S. Appl. No. 61/232,223, filed Aug. 7, 2009, Webster.
U.S. Appl. No. 61/327,855, filed Apr. 26, 2010, Boebel.
U.S. Appl. No. 61/746,837, filed Dec. 28, 2012, Lorsbach.
U.S. Appl. No. 61/747,128, filed Dec. 28, 2012, Lorsbach.
U.S. Appl. No. 61/747,683, filed Dec. 31, 2012, Lorsbach.
U.S. Appl. No. 61/922,572, filed Dec. 31, 2013, Choy.
U.S. Appl. No. 61/922,582, filed Dec. 31, 2013, Choy.
U.S. Appl. No. 61/922,616, filed Dec. 31, 2013, Owen.
U.S. Appl. No. 61/922,630, filed Dec. 31, 2013, Owen.
U.S. Appl. No. 61/922,640, filed Dec. 31, 2013, Owen.
U.S. Appl. No. 62/096,301, filed Dec. 23, 2014, Klittich.
Sep. 28, 2021 First Examination Report issued by the Indian Patent Office in connection with Indian Patent Application No. 202017004086.
Nov. 9, 2021 Office Action issued by the Australian Patent Office in connection with Australian Patent Application No. 2018320492.
Dec. 19, 2021 Office Action issued by the Israeli Patent Office in connection with Israeli Patent Application No. 2971950, including English translation.
Feb. 28, 2022 Office Action issued by the European Patent Office in connection with European Patent Application No. 18765708.5.
Caira Ed.—Montchamp, Jean-Luc. "Crystalline Polymorphism in Organic Compounds." Topics in Current Chemistry; [Topic in Current Chemistry], Springer, Berlin, DE, vol. 198, Jan. 1, 1998, pp. 163-208.

(56) References Cited

OTHER PUBLICATIONS

Harwood, L.M. et al. "Experimental organic chemistry—Principles and practice", Jan. 1, 1989, Experimental Chemistry—Organic Chemistry and Reaction, pp. 127-132.
PCT International Application No. PCT/US2014/072745, published as WO 2015/103259 on Jul. 9, 2015.
PCT International Application No. PCT/US2014/072747, published as WO 2015/103261 on Jul. 9, 2015.
PCT International Application No. PCT/US2014/072748, published as WO 2015/103262 on Jul. 9, 2015.
PCT International Application No. PCT/2015/066756, published as WO 2016/106138 on Jun. 30, 2016.
Mar. 22, 2022 Office Action issued by the Argentinian Patent Office in connection with Argentinian Patent Application No. 20180101983, including English translation.
U.S. Appl. No. 61/232,177, filed Aug. 7, 2009 (Boebel et al.).
U.S. Appl. No. 61/232,204, filed Aug. 7, 2009 (Webster et al.).
U.S. Appl. No. 61/232,223, filed Aug. 7, 2009 (Webster et al.).
U.S. Appl. No. 61/232,232, filed Aug. 7, 2009 (Pobanz).
U.S. Appl. No. 61/232,245, filed Aug. 7, 2009 (Pobanz).
U.S. Appl. No. 61/327,855, filed Apr. 26, 2010 (Boebel et al.).
U.S. Appl. No. 61/524,506, filed Aug. 17, 2011 (Boebel).
U.S. Appl. No. 61/746,837, filed Dec. 28, 2012 (Lorsbach et al.).
U.S. Appl. No. 61/747,128, filed Dec. 28, 2012 (Lorsbach et al.).
U.S. Appl. No. 61/747,683, filed Dec. 31, 2012 (Lorsbach et al.).
U.S. Appl. No. 61/922,572, filed Dec. 31, 2013 (Choy et al.).
U.S. Appl. No. 61/922,582, filed Dec. 31, 2013 (Choy et al.).
U.S. Appl. No. 61/922,616, filed Dec. 31, 2013 (Owen et al.).
U.S. Appl. No. 61/922,630, filed Dec. 31, 2013 (Owen et al.).
U.S. Appl. No. 61/922,640, filed Dec. 31, 2013 (Owen et al.).
U.S. Appl. No. 62/096,301, filed Dec. 23, 2014 (Klittich et al.).

\* cited by examiner

POLYMORPHS OF 5-FLUORO-4-IMINO-3-METHYL-1-TOSYL-3,4-DIHYDROPYRIMIDIN-2-ONE

This application claims priority of U.S. Provisional Application No. 62/533,509, filed Jul. 17, 2017, the contents of which are hereby expressly incorporated by reference.

Throughout this application various publications are referenced. The disclosures of these documents in their entireties are hereby incorporated by reference into this application in order to more fully describe the state of the art to which this invention pertains.

BACKGROUND

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop, and consequently, increase the value of the crop. In most situations, the increase in value of the crop is worth at least three times the cost of the use of the fungicide. 5-fluoro-4-imino-3-methyl-1-tosyl-3,4-dihydropyrimidin-2(1H)-one is a fungicide which provides control of a variety of pathogens in economically important crops including, but not limited to, the causal agent of leaf blotch in wheat, *Septoria tritici*, (SEPTTR) and diseases caused by fungi of the classes Ascomycetes and Basidiomycetes.

The present invention provides a crystalline form of the compound having the following structure:

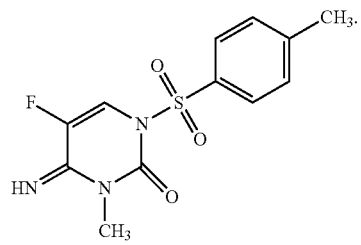

The present invention also provides a fungicidal composition comprising a solution of the compound having the structure:

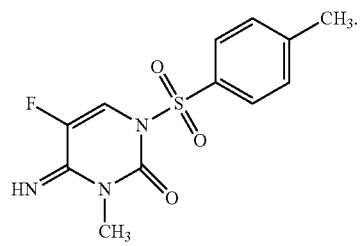 [SMILES: Cc1ccc(S(=O)(=O)n2cc(F)c(=N)n(C)c2=O)cc1]

The present invention further provides a method for control of fungal attack on roots and/or seeds and/or a plant, the method comprising:

i) obtaining a solution of the compound having the structure:

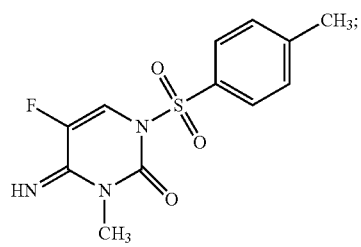 [SMILES: Cc1ccc(S(=O)(=O)n2cc(F)c(=N)n(C)c2=O)cc1]

and ii) applying the solution to the roots, seeds or foliage of the plant, to a locus in which the infestation is to be prevented, and/or to the plant, so as to thereby control fungal attack on the roots and/or seeds and/or plant.

The present invention yet further provides a method for the control of fungal attack on a plant, the method comprising:

i) obtaining a crystalline form of the compound having the following structure:

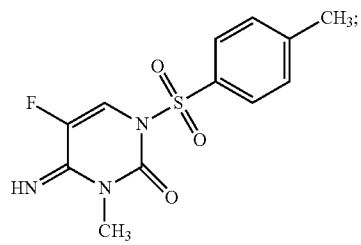 [SMILES: Cc1ccc(S(=O)(=O)n2cc(F)c(=N)n(C)c2=O)cc1]

and ii) applying the crystalline form to a locus of the fungus, to a locus in which the infestation is to be prevented, and/or to the plant, so as to thereby control fungal attack on the plant.

DETAILED DESCRIPTION

The present invention relates to crystalline forms of 5-fluoro-4-imino-3-methyl-1-tosyl-3,4-dihydropyrimidin-2 (1H)-one, which has the following structure:

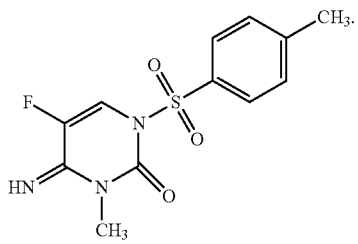

In one embodiment, an anhydrous crystalline form of 5-fluoro-4-imino-3-methyl-1-tosyl-3,4-dihydropyrimidin-2 (1H)-one.

In one embodiment, a polymorph of 5-fluoro-4-imino-3-methyl-1-tosyl-3,4-dihydropyrimidin-2(1H)-one.

In one embodiment, a hydrate of 5-fluoro-4-imino-3-methyl-1-tosyl-3,4-dihydropyrimidin-2(1H)-one.

In one embodiment, a solvate of 5-fluoro-4-imino-3-methyl-1-tosyl-3,4-dihydropyrimidin-2(1H)-one.

In one embodiment, wherein the solvate contains 1,4-dioxane.

In one embodiment, wherein the solvate contains tetrahydrofuran.

In one embodiment, wherein the solvate contains ethyl acetate.

In one embodiment, a pseudopolymorph of 5-fluoro-4-imino-3-methyl-1-tosyl-3,4-dihydropyrimidin-2(1H)-one.

These polymorphs, solvates and hydrates forms exhibit distinct spectral characteristics as depicted by their X-ray diffraction patterns, Differential Scanning calorimetry (DSC) thermograms and FTIR thermograms.

Figure 1:
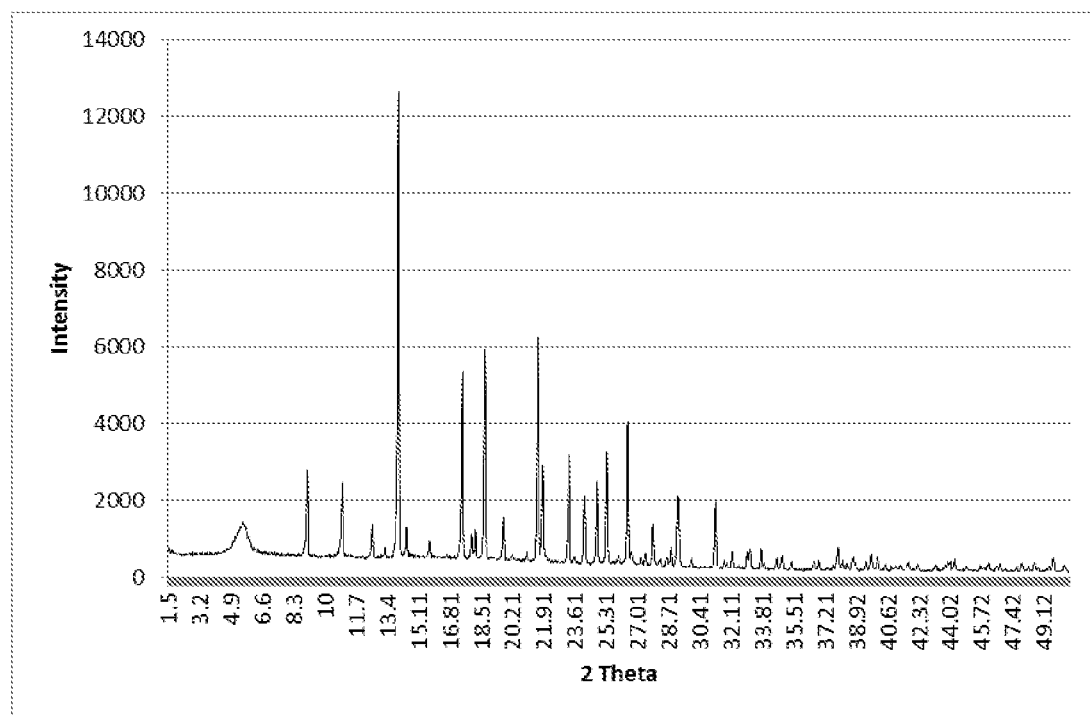
FIG. 1: X-ray powder diffraction spectrum of Form I.

In one embodiment, the present invention provides a crystalline polymorphic form designated "Form I". Form I exhibits an X-ray powder diffraction pattern as shown in FIG. 1, having characteristic peaks at 2-theta angles of 9.08, 10.98, 14.05, 17.51, 18.75, 21.63, 23.33, 24.70, 24.83, 25.37, 26.51 and 29.23. In one embodiment, the powder X-ray diffraction pattern of Form I comprises characteristic peaks at 2-theta angles of 14.05, 17.51, 18.75, 21.63 and 26.51. In one embodiment, the powder X-ray diffraction pattern of Form I comprises characteristic peaks at 2-theta angles of 14.05, 17.51, 18.75 and 21.63.

Figure 2:
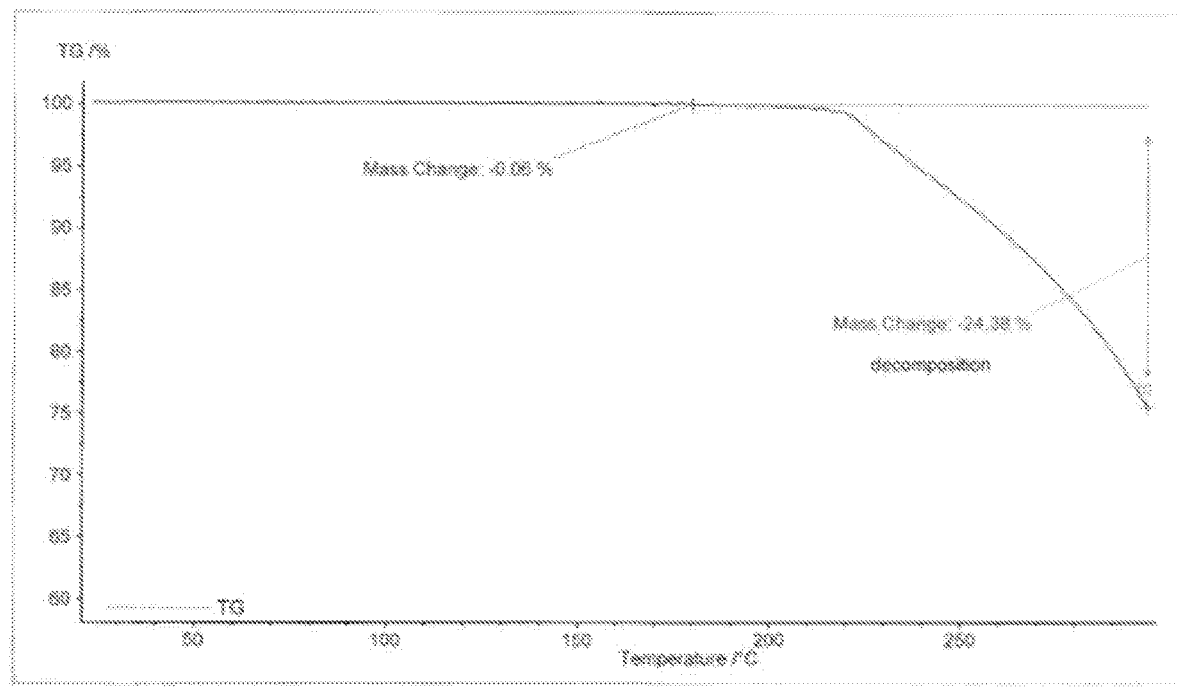
FIG. 2: TG-FTIR of Form I.

Form I also exhibits a TG-FTIR thermogram as shown in FIG. 2, which is characterized by decomposition beginning at a temperature greater than 210° C.

Figure 3:
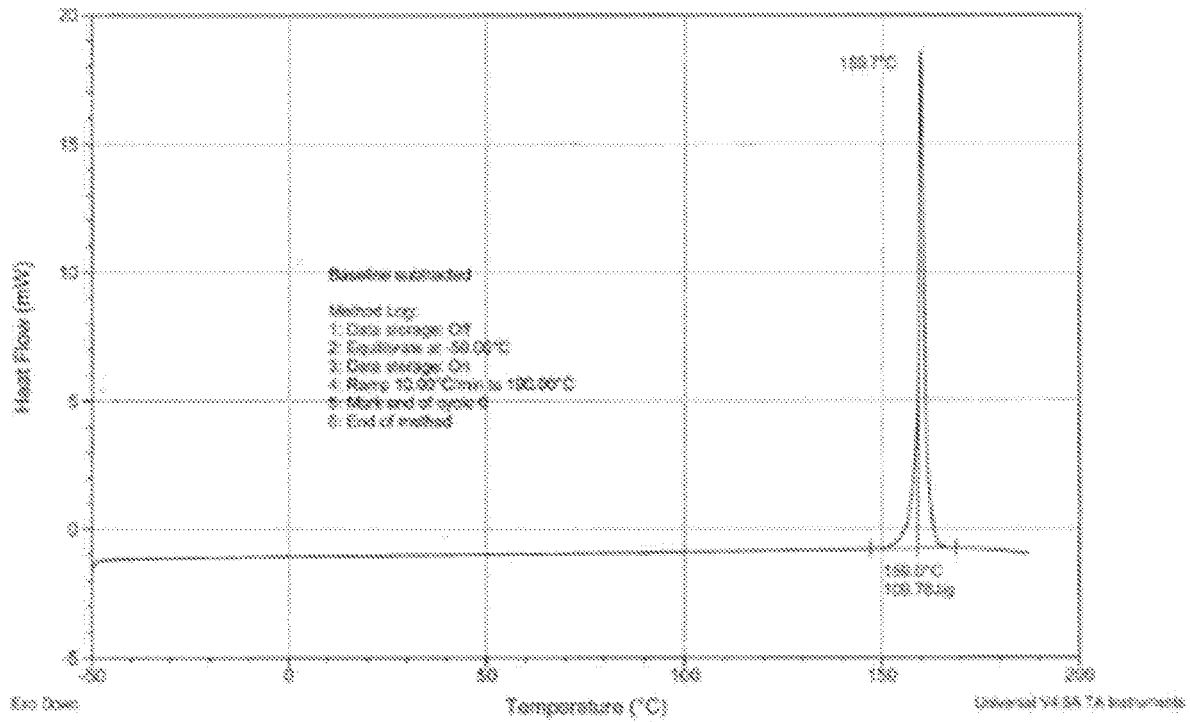
FIG. 3: Differential Scanning calorimetry (DSC) thermogram of Form I.

Form I also exhibits a Differential Scanning calorimetry (DSC) thermogram as shown in FIG. 3, which is characterized by a predominant endothermic peak with a peak temperature of about 160° C., a predominant endothermic peak with an onset temperature of about 159° C., and a predominant endothermic peak with a melting enthalpy of about 110 J/g.

Figure 4:
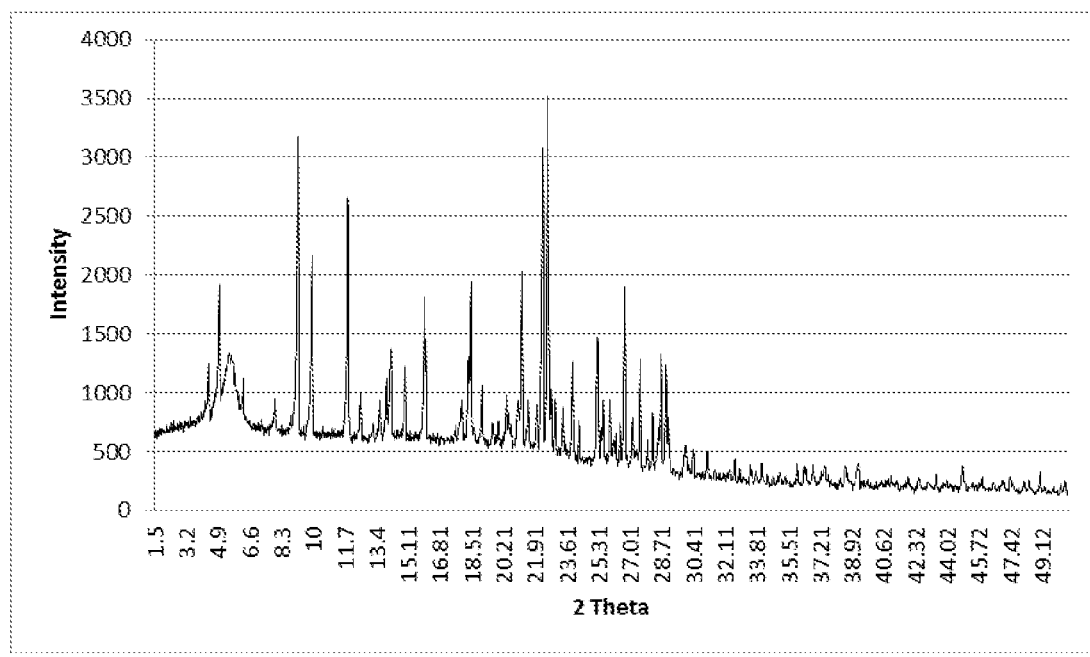
FIG. 4: An X-ray powder diffraction spectrum of Form II.

In one embodiment, the present invention provides a crystalline polymorphic form designated "Form II". Form II exhibits an X-ray powder diffraction pattern as shown in FIG. 4, having characteristic peaks at 2-theta angles of 7.98, 9.20, 9.96, 11.88, 15.99, 18.49, 21.23, 22.33, 22.59, 26.73. In one embodiment, the powder X-ray diffraction pattern of Form II comprises characteristic peaks at 2-theta angles of 9.20, 9.96, 11.88, 22.33 and 22.59. In one embodiment, the powder X-ray diffraction pattern of Form II comprises characteristic peaks at 2-theta angles of 9.20, 11.88, 22.33 and 22.59.

Figure 5:
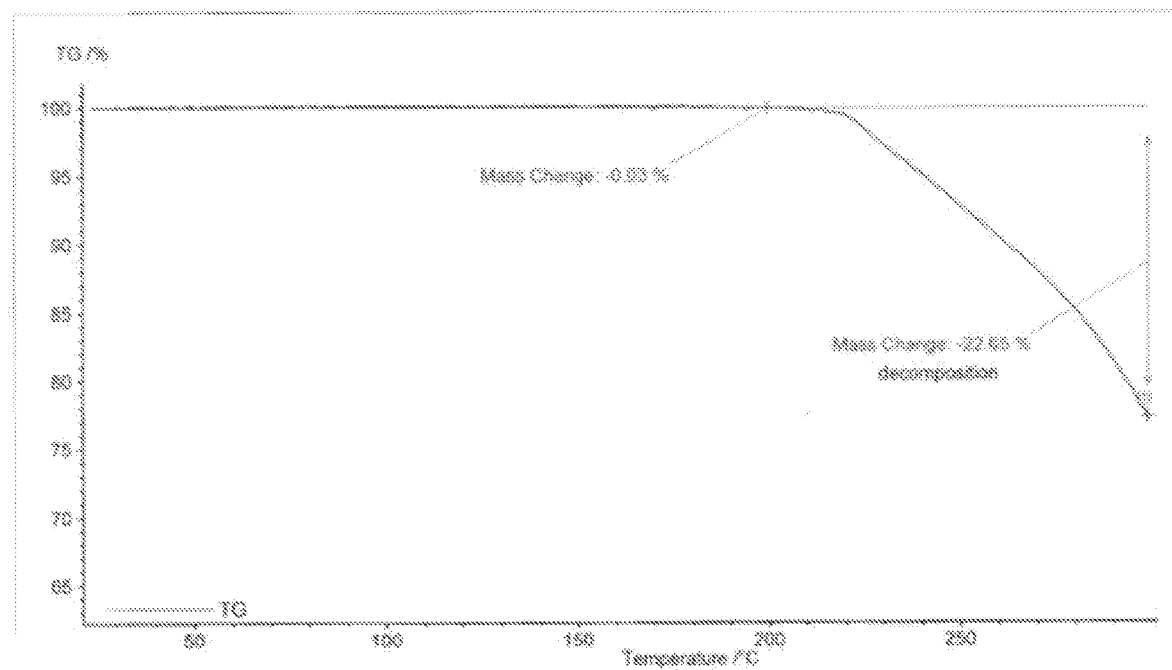
FIG. 5: TG-FTIR of Form II.

Form II also exhibits a TG-FTIR thermogram as shown in FIG. 5, which is characterized by decomposition beginning at a temperature greater than 210° C.

Figure 6:
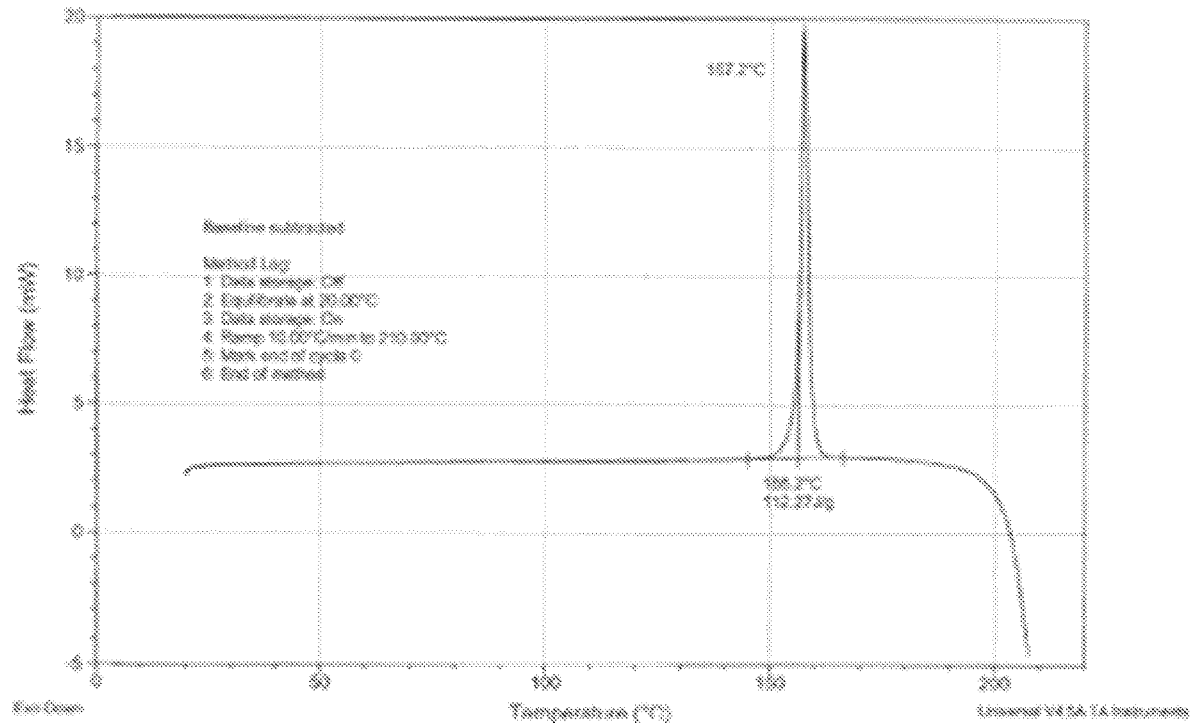
FIG. 6: Differential Scanning calorimetry (DSC) thermogram of Form II.

Form II also exhibits a Differential Scanning calorimetry (DSC) thermogram as shown in FIG. 6, which is characterized by a predominant endothermic peak with a peak temperature of about 157° C., a predominant endothermic peak with an onset temperature of about 156° C., and a predominant endothermic peak with a melting enthalpy of about 112 J/g.

Figure 7:
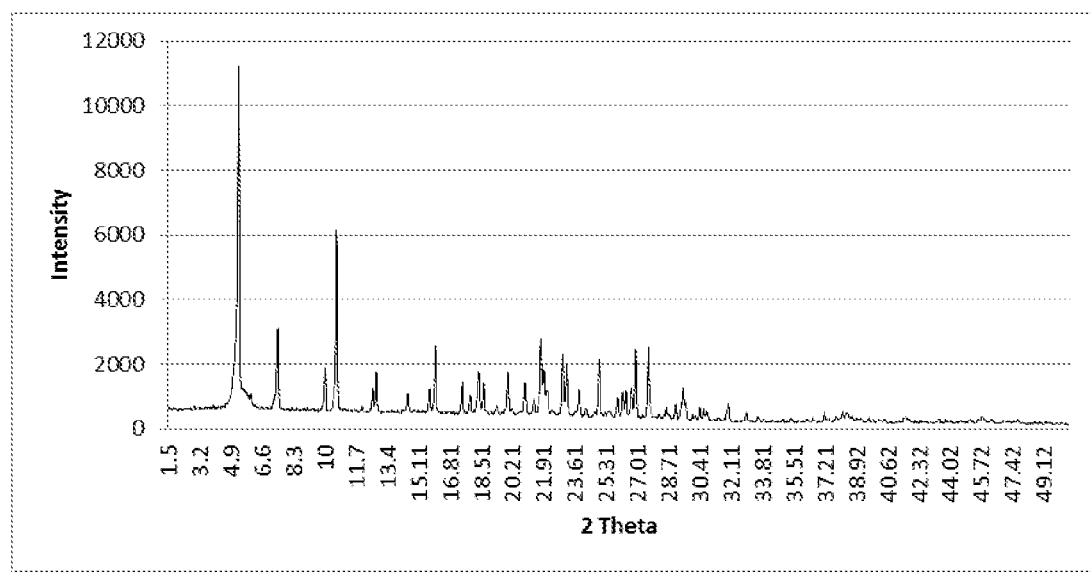
FIG. 7: X-ray powder diffraction spectrum of Hydrate.

In one embodiment, the present invention provides a crystalline hydrate form designated "Hydrate". Hydrate exhibits an X-ray powder diffraction pattern as shown in FIG. 7, having characteristic peaks at 2-theta 5.34, 7.48, 10.68, 16.05, 21.79, 22.99, 23.19, 24.95, 26.95, 27.63. In one embodiment, the powder X-ray diffraction pattern of Hydrate comprises characteristic peaks at 2-theta angles of 5.34, 7.48, 10.68, 16.05 and 21.79. In one embodiment, the powder X-ray diffraction pattern of Hydrate comprises characteristic peaks at 2-theta angles of 5.34, 7.48, 10.68 and 16.05.

Figure 8:
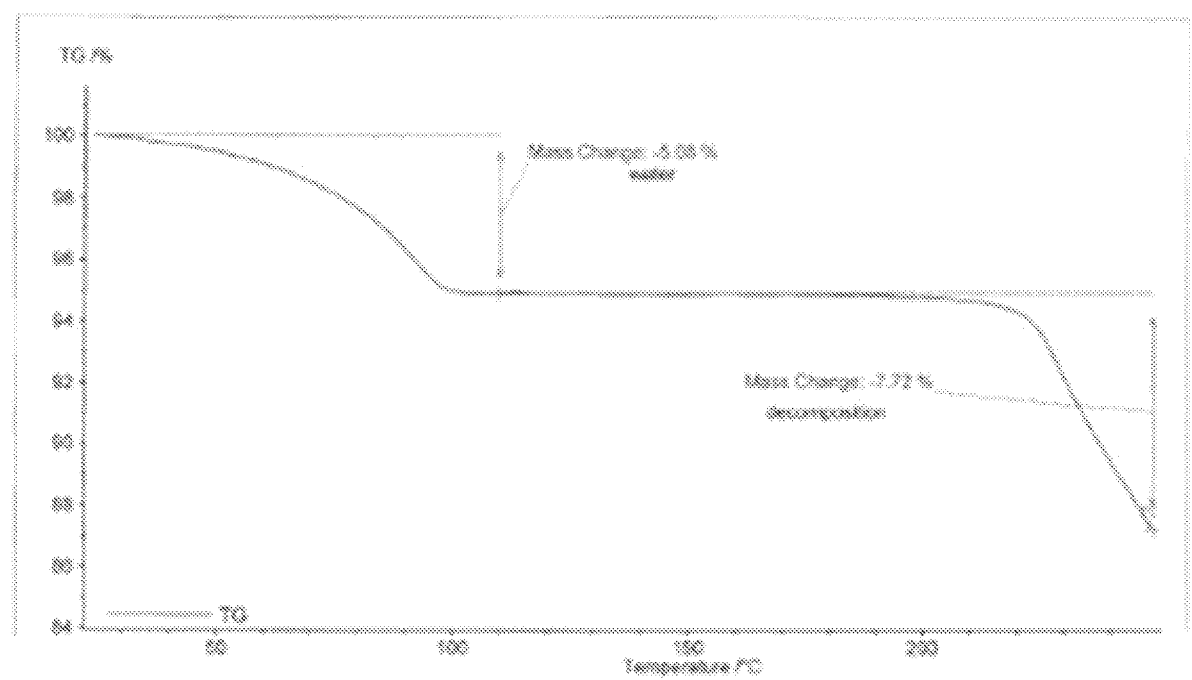
FIG. 8: TG-FTIR of Hydrate.

Hydrate also exhibits a TG-FTIR thermogram as shown in FIG. 8, which is characterized by decomposition beginning at a temperature greater than 190° C.

Figure 9:
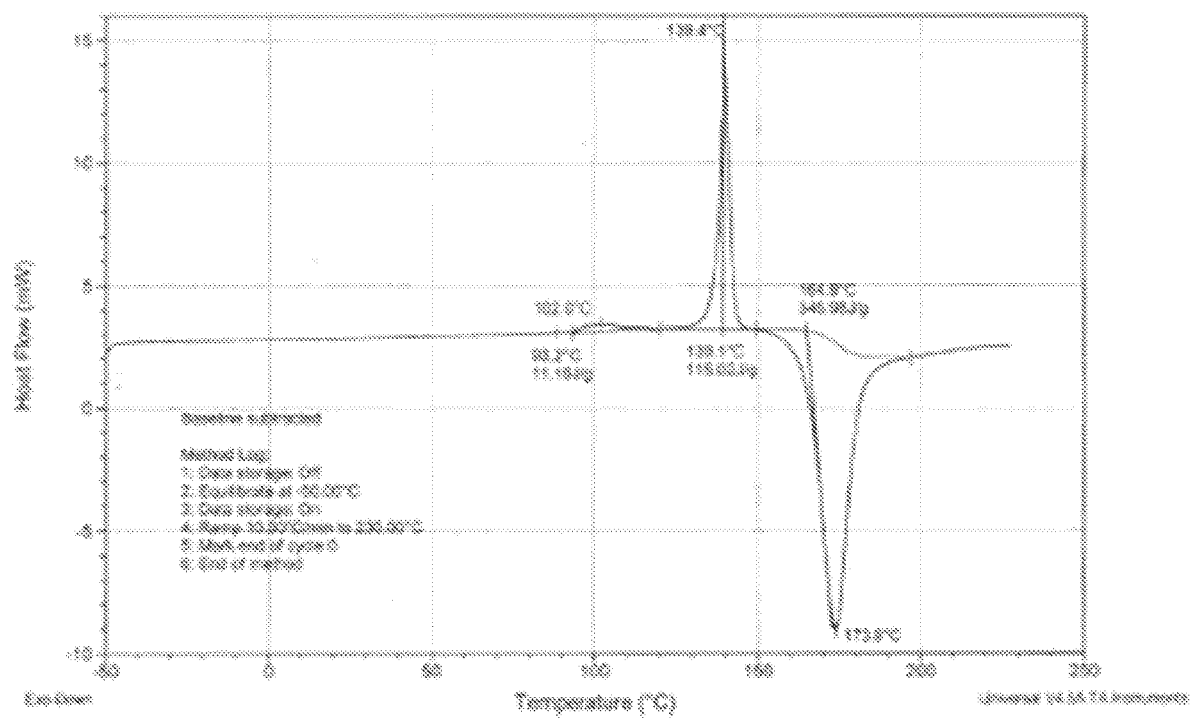
FIG. 9: Differential Scanning calorimetry (DSC) thermogram of Hydrate (closed pan).

Hydrate also exhibits a Differential Scanning calorimetry (DSC) thermogram as shown in FIG. 9, which is characterized by a predominant endothermic peak with a peak temperature of about 139.5° C., a predominant endothermic peak with an onset temperature of about 139° C., and a predominant endothermic peak with a melting enthalpy of about 115 J/g, wherein the DSC is measured in a sealed pan.

Figure 10:
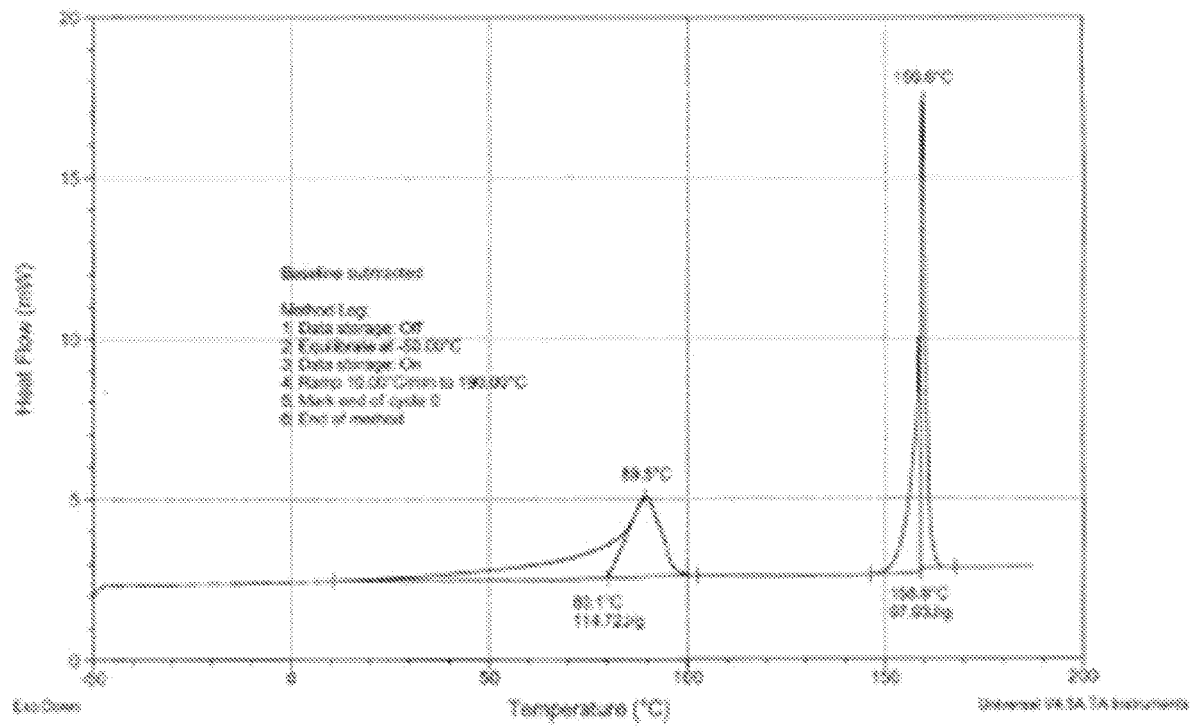
FIG. 10: Differential Scanning calorimetry (DSC) thermogram of Hydrate (open pan).

Hydrate also exhibits a Differential Scanning calorimetry (DSC) thermogram as shown in FIG. 10, which is characterized by a predominant endothermic peak with a peak temperature of about 160° C., a predominant endothermic peak with an onset temperature of about 159° C., and a predominant endothermic peak with a melting enthalpy of about 98 J/g, wherein the DSC is measured in an open pan.

Figure 11:
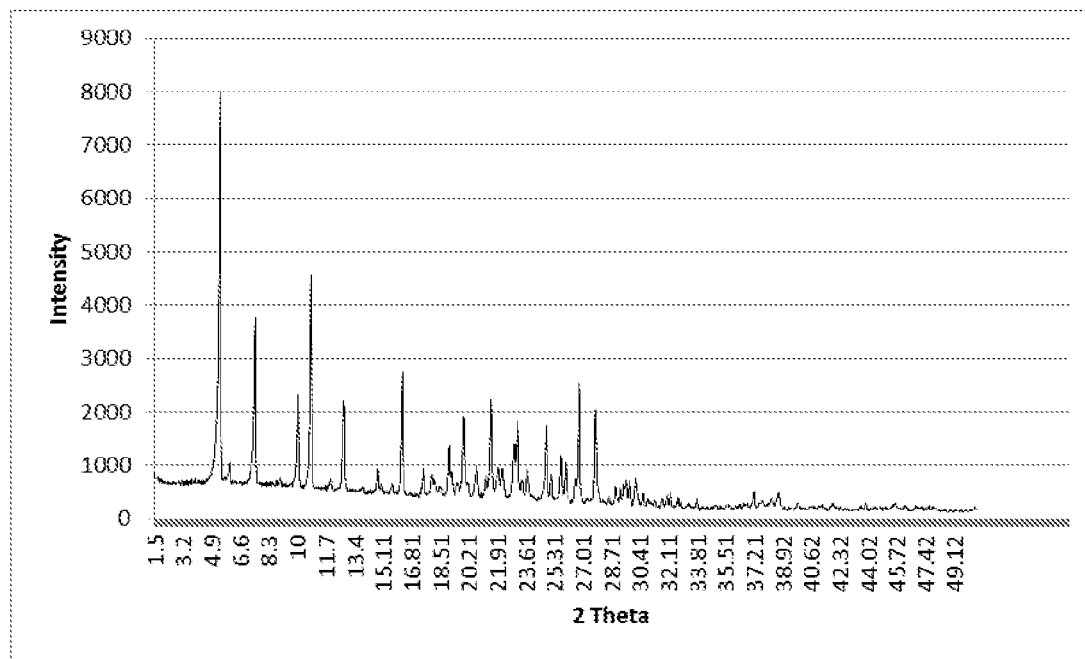
FIG. 11: X-ray powder diffraction spectrum of Solvate S5.

In one embodiment, the present invention provides a crystalline solvate form designated "Form S5". Form S5 exhibits an X-ray powder diffraction pattern as shown in FIG. 11, having characteristic peaks at 2-theta 5.42, 7.50, 10.06, 10.82, 12.80, 16.91, 21.55, 23.13, 24.83, 26.81, 27.77. In one embodiment, the powder X-ray diffraction pattern of Form S5 comprises characteristic peaks at 2-theta angles of 5.42, 7.50, 10.06, 10.82, and 16.91. In one embodiment, the powder X-ray diffraction pattern of Form S5 comprises characteristic peaks at 2-theta angles of 5.42, 7.50, 10.82 and 16.91.

Figure 12:
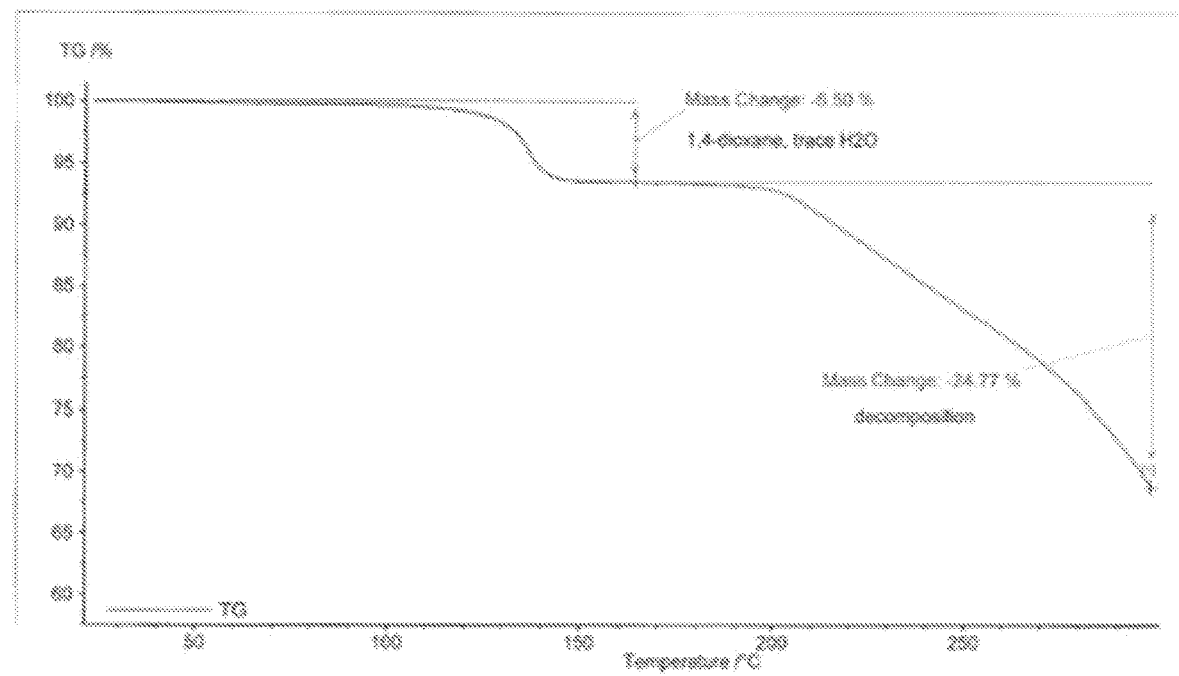
FIG. 12: TG-FTIR thermogram of Solvate S5.

Form S5 also exhibits a TG-FTIR thermogram as shown in FIG. 12, which is characterized by decomposition beginning at a temperature greater than 180° C.

Figure 13:
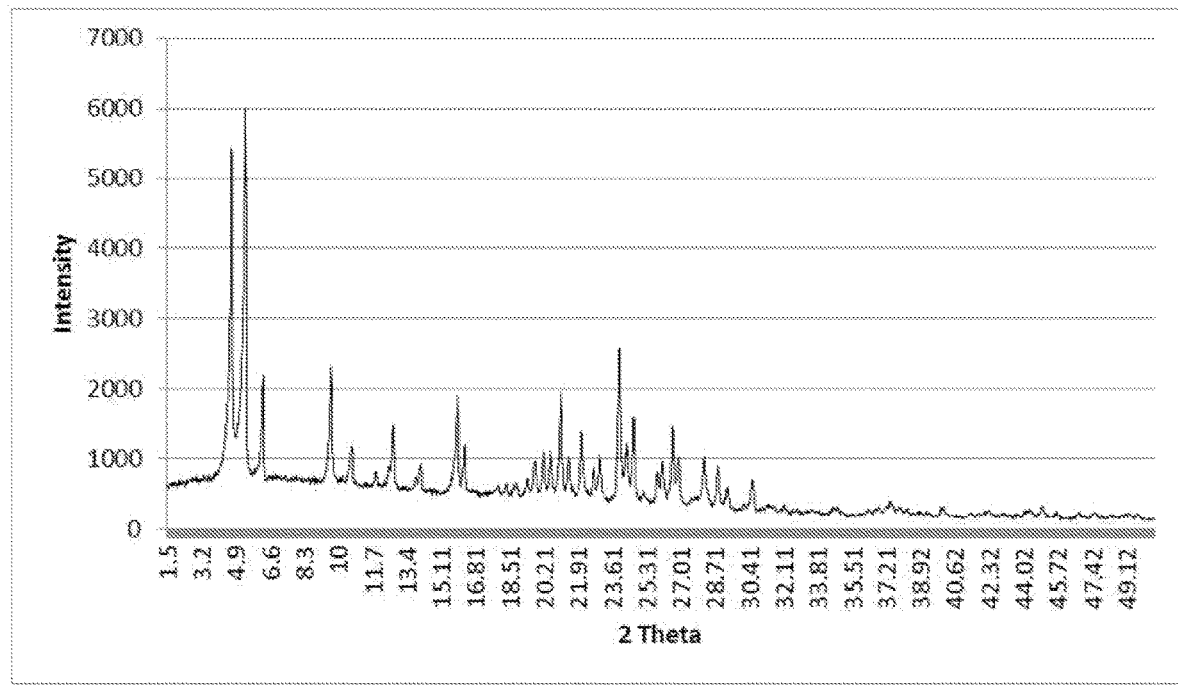
FIG. 13: X-ray powder diffraction spectrum of Solvate S8.

In one embodiment, the present invention provides a crystalline solvate form designated "Form S8". Form S8 exhibits an X-ray powder diffraction pattern as shown in FIG. 13, having characteristic peaks at 2-theta 4.7, 5.00, 5.38, 6.26, 9.66, 15.93, 21.05, 23.97, 24.69. In one embodiment, the powder X-ray diffraction pattern of Form S8 comprises characteristic peaks at 2-theta angles of 4.7, 5.00, 5.38, 6.26, 9.66 and 23.97. In one embodiment, the powder X-ray diffraction pattern of Form S8 comprises characteristic peaks at 2-theta angles of 4.7, 5.00, 9.66 and 23.97.

Figure 14:
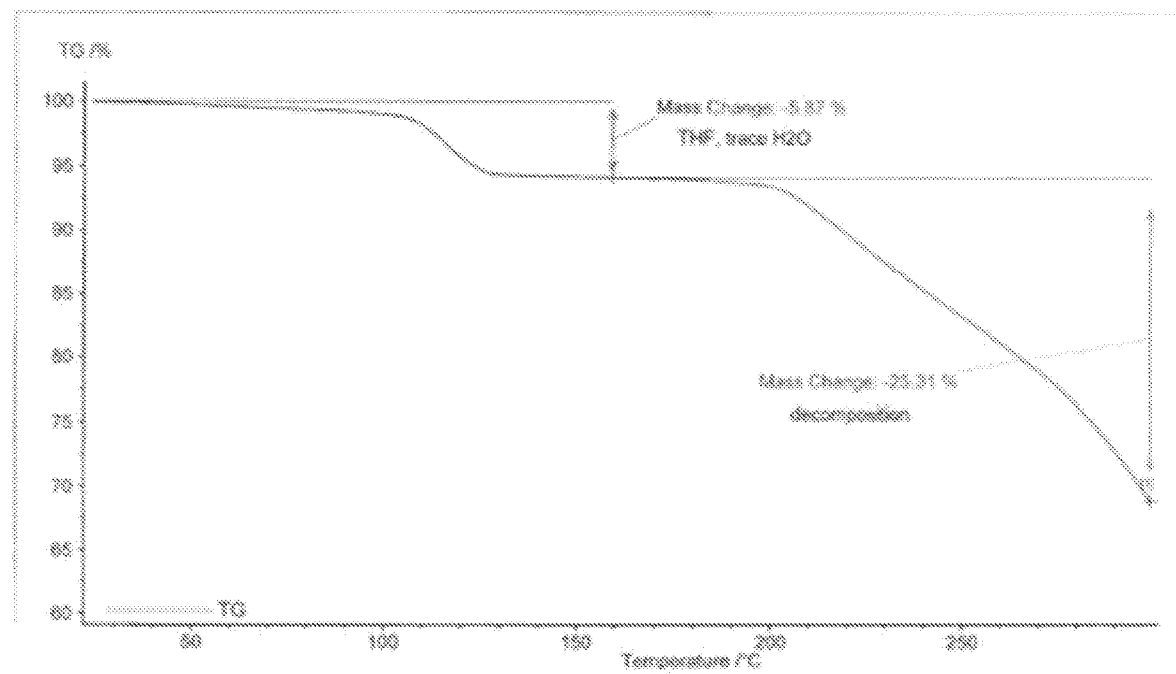
FIG. 14: TG-FTIR thermogram of Solvate S8.

Form S8 also exhibits a TG-FTIR thermogram as shown in FIG. 14, which is characterized by decomposition beginning at a temperature greater than 180° C.

Figure 15:
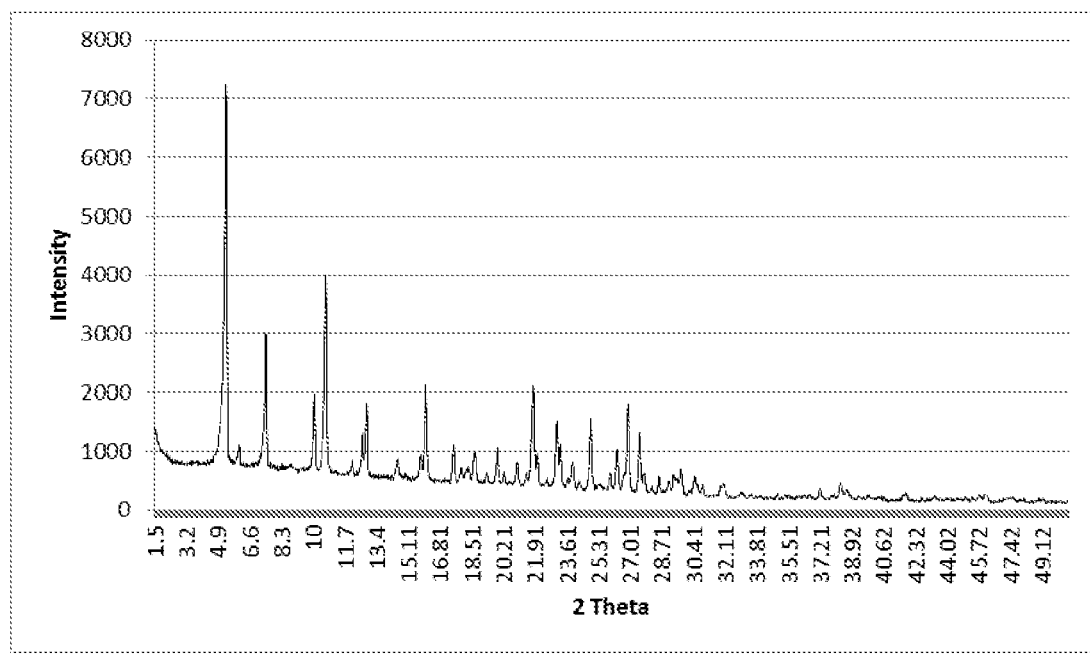
FIG. 15: X-ray powder diffraction spectrum of Solvate S1.

In one embodiment, the present invention provides a crystalline solvate form designated "Form S1". Form S1 exhibits an X-ray powder diffraction pattern as shown in FIG. 15, having characteristic peaks at 2-theta 5.34, 7.48, 10.10, 10.68, 12.90, 16.07, 21.83, 23.09, 24.91, 26.93. In one embodiment, the powder X-ray diffraction pattern of Form S1 comprises characteristic peaks at 2-theta angles of 5.34, 7.48, and 10.68. In one embodiment, the powder X-ray diffraction pattern of Form S1 comprises characteristic peaks at 2-theta angles of 5.34, 7.48, 10.68 and 21.83. In one embodiment, the powder X-ray diffraction pattern of Form S1 comprises characteristic peaks at 2-theta angles of 5.34, 7.48, 10.68, 16.07 and 21.83.

Figure 16:
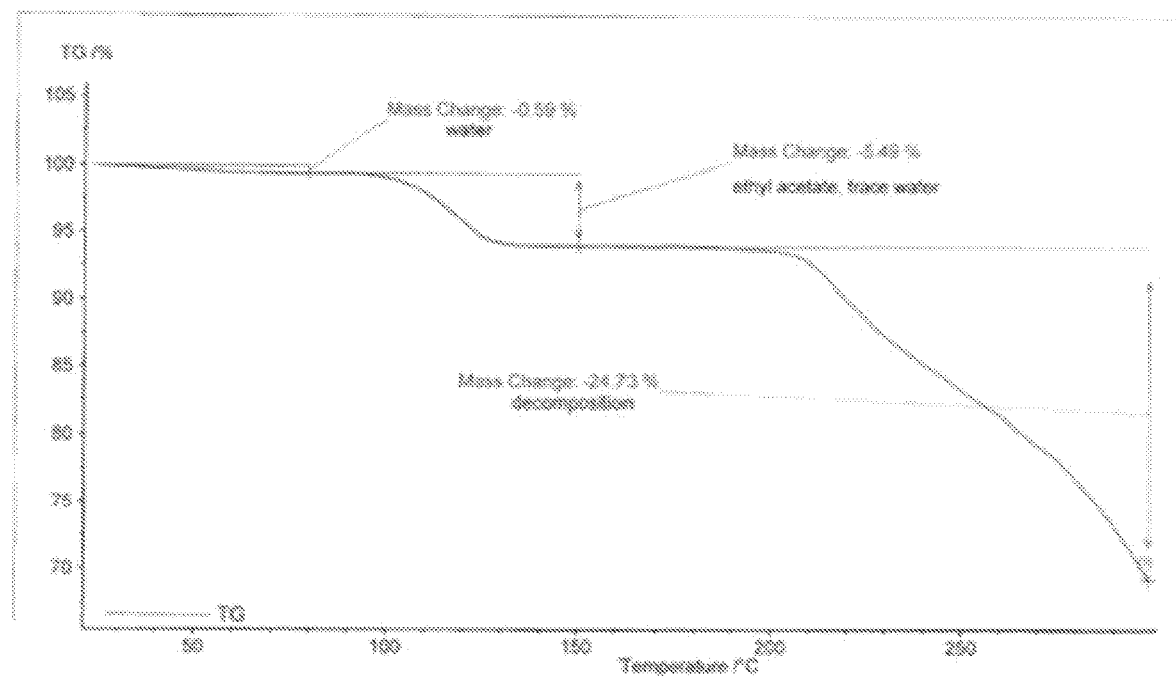
FIG. 16: TG-FTIR thermogram of Solvate S1.

Form S1 also exhibits a TG-FTIR thermogram as shown in FIG. 16, which is characterized by decomposition beginning at a temperature greater than 200° C.

In some embodiments, a mixture of crystalline forms of the compound having the following structure:

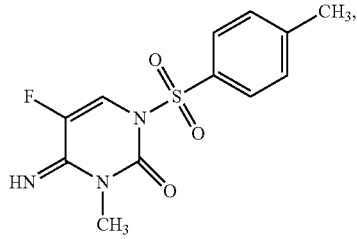

which is a mixture of one or more crystalline forms of the present invention.

In some embodiments, a mixture of crystalline forms of the compound having the following structure:

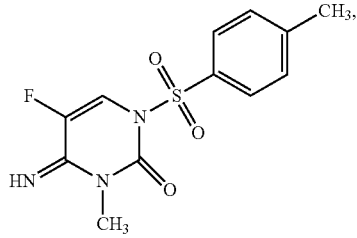

which is a mixture of one or more anhydrous crystalline forms of the present invention.

In some embodiments, a mixture of crystalline forms of the compound having the following structure:

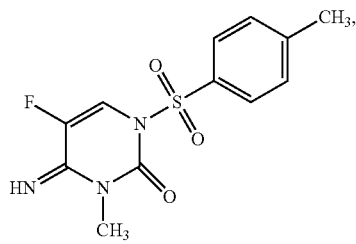

which is a mixture of the crystalline form I and the crystalline form II.

In some embodiments; the mixture is at least 25% the crystalline form I.

In some embodiments, the mixture is at least 50% the crystalline form I.

In some embodiments, the mixture is at least 75% the crystalline form I.

In some embodiments, a mixture of crystalline forms of the compound having the following structure:

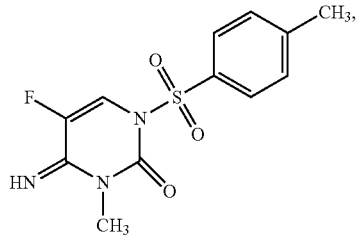 [SMILES: Cc1ccc(S(=O)(=O)n2cc(F)c(=N)n(C)c2=O)cc1]

which is a mixture of the crystalline form I and the crystalline Hydrate form.

In some embodiments, the mixture is at least 25% the crystalline form I.

In some embodiments, the mixture is at least 50% the crystalline form I.

In some embodiments, the mixture is at least 75% the crystalline form I.

In some embodiments, a mixture of crystalline forms of the compound having the following structure:

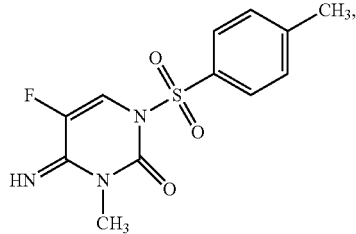

which is a mixture of the crystalline form II and the crystalline Hydrate form.

In some embodiments, the mixture is at least 25% the crystalline form II.

In some embodiments, the mixture is at least 50% the crystalline form II.

In some embodiments, the mixture is at least 75% the crystalline form II.

In some embodiments, a fungicidal mixture comprising one or more crystalline forms of the present invention.

In some embodiments, a fungicidal mixture comprising the crystalline polymorph, solvate or hydrate of the present invention.

In some embodiments, a fungicidal mixture is provided including a fungicidally effective amount of the polymorph, solvate, or hydrate of the present invention.

In some embodiments, a fungicidal mixture comprising the crystalline polymorph, solvate, or hydrate of the present invention and one or more fungicidal carriers.

In some embodiments, the crystalline polymorph, solvate or hydrate of the present invention is mixed with at least one least additional fungicide.

In some embodiments, the crystalline polymorph, solvate or hydrate of the present invention is mixed with at least one excipient.

In some embodiments, a fungicidal mixture of the present invention further comprising at least one additional fungicide.

In some embodiments, the mixture or fungicidal mixture of the present invention is a tank mix.

In some embodiments, the components of the mixture or fungicidal mixture of the present invention are applied separately.

In some embodiments, the components of the mixture or fungicidal mixture of the present invention are applied simultaneously.

In some embodiments, the components of the mixture or fungicidal mixture of the present invention are applied together as a single composition.

In some embodiments, the components of the mixture or fungicidal mixture of the present invention are applied in separate compositions.

In some embodiments, the tank mix comprises one or more crystalline forms of the present invention and at least one other pesticidal compound.

In some embodiments, the tank mix further comprises at least one excipient.

In some embodiments, the mixture or fungicidal mixture of the present invention is a solid mixture.

In some embodiments, the mixture or fungicidal mixture of the present invention is a liquid mixture.

In some embodiments, a fungicidal mixture of the present invention further comprising at least one additional fungicide.

In some embodiments, a composition comprising the crystalline polymorph, solvate or hydrate of the present invention.

In some embodiments, a fungicidal composition comprising the crystalline polymorph, solvate or hydrate of the present invention.

In some embodiments, a composition comprising the mixture of the present invention.

In some embodiments, a fungicidal composition comprising the mixture of the present invention.

In some embodiments, a fungicidal composition is provided including a fungicidally effective amount of the polymorph, solvate, hydrate or mixture of the present invention.

In some embodiments, a fungicidal composition comprising the crystalline polymorph, solvate, hydrate or mixture of the present invention and one or more fungicidal carriers.

In some embodiments, the composition or fungicidal composition further comprises at least one excipient.

In some embodiments, the composition or fungicidal composition further comprises at least one excipient for preparation of a tank mix.

In some embodiments, the composition or fungicidal composition of the present invention is a solid composition.

In some embodiments, the composition or fungicidal composition of the present invention is a liquid composition.

In some embodiments, a fungicidal composition of the present invention further comprising at least one additional fungicide.

In some embodiments, wherein the at least one additional fungicide is a fungicidal sterol biosynthesis inhibitor.

In some embodiments, wherein the sterol biosynthesis inhibitor is selected from the group consisting of prothioconazole, epoxiconazole, cyproconazole, myclobutanil, prochloraz, metconazole, difenoconazole, tebuconazole, tetraconazole, fenbuconazole, propiconazole, fluquinconazole, flusilazole, flutriafol, and fenpropimorph.

In some embodiments, wherein the sterol biosynthesis inhibitor is selected from the group consisting of epoxiconazole, cyproconazole, myclobutanil, metconazole, propiconazole, prothioconazole, fluquinconazole, flutriafol, and difenoconazole.

In some embodiments, wherein the at least one additional fungicide is a succinate dehydrogenase inhibitor.

In some embodiments, wherein the succinate dehydrogenase inhibitor is selected from the group consisting of fluxapyroxad, benzovindiflupyr, penthiopyrad, isopyrazam, bixafen, boscalid, penflufen, and fluopyram.

In some embodiments, wherein the succinate dehydrogenase inhibitor is selected from the group consisting of fluxapyroxad, benzovindiflupyr, penthiopyrad, isopyrazam, boscalid, and fluopyram.

In some embodiments, wherein the at least one additional fungicide is a strobilurin fungicide.

In some embodiments, wherein the strobilurin fungicide is selected from the group consisting of pyraclostrobin, fluoxastrobin, azoxystrobin, trifloxystrobin, picoxystrobin, and kresoxim-methyl.

In some embodiments, wherein the at least one additional fungicide is a fungicidal multisite inhibitor.

In some embodiments, wherein the fungicidal multisite inhibitor is selected from a group consisting of chlorothalonil, mancozeb, folpet, and captan.

In some embodiments, wherein the fungicidal multisite inhibitor is folpet or captan.

In some embodiments, the crystalline polymorph, solvate or hydrate of the present invention alone, or the crystalline polymorph, solvate or hydrate of the present invention in combination with at least one additional fungicide provides control of a fungal pathogen and the fungal pathogen is one of Leaf Blotch of Wheat (*Mycosphaerella graminicola*; anamorph: *Septoria tritici*), Wheat Brown Rust (*Puccinia triticina*), Stripe Rust (*Puccinia striiformis* f. sp. *tritici*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

In some embodiments, the fungus is one of Leaf Blotch of Wheat (*Mycosphaerella graminicola*; anamorph: *Septoria tritici*), Wheat Brown Rust (*Puccinia triticina*), Stripe Rust (*Puccinia striiformis* f. sp. *tritici*), Scab of Apple (*Venturia* inaequalis), Blister Smut of Maize (*Ustilago maydis*), Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

In some embodiments, a method for the control of fungal attack on a plant, the method comprising:

i) obtaining a crystalline form of the compound having the following structure:

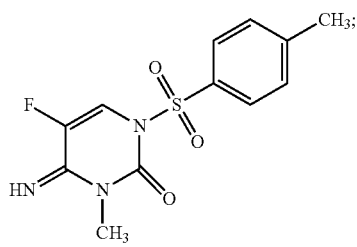

and ii) applying the crystalline form to a locus of the fungus, to a locus in which the infestation is to be prevented, and/or to the plant, so as to thereby control fungal attack on the plant.

In some embodiments, a method for the control of fungal attack on a plant, the method comprising applying the crystalline form, mixture or composition the present invention to a locus of the fungus, to a locus in which the infestation is to be prevented, and/or to the plant, so as to thereby control fungal attack on the plant.

In some embodiments, a method for the control of fungal attack on a plant, the method comprising applying a synergistic, fungicidal mixture to a locus of the fungus, to a locus in which the infestation is to be prevented, and/or to the plant, the mixture comprising: i) a fungicidally effective amount of the crystalline form, mixture or composition the present invention; and ii) at least one additional fungicide, so as to thereby control fungal attack on the plant.

In some embodiments, a method for the control of fungal attack on roots and/or seeds and/or a plant, the method comprising applying the crystalline form of, the mixture of or the composition of the present invention, to the roots, seeds or foliage of plants, to a locus in which the infestation is to be prevented, and/or to the plant, so as to thereby control fungal attack on the roots and/or seeds and/or plant.

In some embodiments, the method wherein the mixture is a tank mix.

In some embodiments, the method wherein the tank mix further comprises at least one excipient.

The present invention also provides a method for the control of fungal attack on roots and/or seeds and/or a plant, the method comprising:

i) obtaining a solution of the compound having the structure:

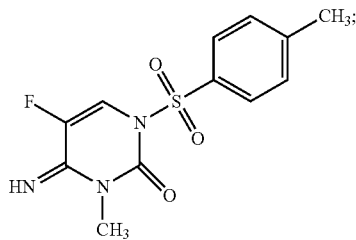

and ii) applying the solution to the roots, seeds or foliage of the plant, to a locus in which the infestation is to be prevented, and/or to the plant, so as to thereby control fungal attack on the roots and/or seeds and/or plant.

The present invention also provides a method for the control of fungal attack on roots and/or seeds and/or plant, the method comprising:

i) obtaining a solution of the crystalline form or of the mixture of the present invention; and ii) applying the solution to the roots, seeds or foliage of plants, to a locus in which the infestation is to be prevented, and/or to the plant, so as to thereby control fungal attack on the plant.

In some embodiments, the method wherein the mixture is a tank mix.

In some embodiments, the method wherein the tank mix further comprises at least one excipient.

The present invention also provides a fungicidal composition comprising the compound having the structure:

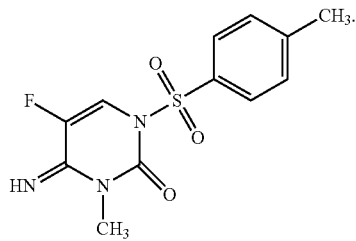 [SMILES: Cc1ccc(S(=O)(=O)n2cc(F)c(=N)n(C)c2=O)cc1]

The present invention also provides a fungicidal composition comprising the crystalline form of present invention or of the mixture of the present invention.

The present invention also provides a method for the control of fungal attack on a plant, the method comprising:

i) obtaining a composition of the compound having the structure:

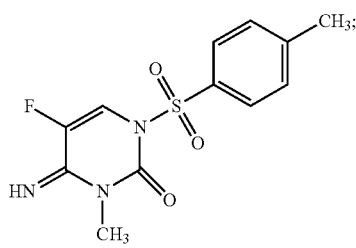

and ii) applying the composition to a locus of the fungus, to a locus in which the infestation is to be prevented, and/or to the plant, so as to thereby control fungal attack on the plant.

The present invention also provides a method for the control of fungal attack on a plant, the method comprising:

i) obtaining a composition of the crystalline form or of the mixture of the present invention; and ii) applying the composition to a locus of the fungus, to a locus in which the infestation is to be prevented, and/or to the plant, so as to thereby control fungal attack on the plant.

The present invention also provides a method for the control of fungal attack on a plant and/or roots and/or seeds, the method comprising:

i) obtaining a composition of the crystalline form or of the mixture of the present invention; and ii) applying the composition to the roots, seeds or foliage of plants for the control of various fungi, without damaging the commercial value of the plants.

The present invention also provides a method for the control of fungal attack on roots and/or seeds and/or plant, the method comprising:

i) obtaining a composition of the compound having the structure:

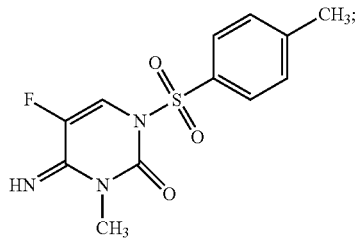

and ii) applying the composition to the roots, seeds or foliage of plants, to a locus in which the infestation is to be prevented, and/or to the plant, so as to thereby control fungal attack on the plant.

In another aspect, the present invention provides processes for preparing polymorphs Form I and Form II; the Hydrate; and Solvate Forms S5, S8 and S1.

In some embodiments, the process wherein the crystalline polymorph, solvate or hydrate is formed by cooling crystallization, evaporation crystallization or suspension crystallization.

In some embodiments, a process for preparing the crystalline polymorph form of Form I, comprising:

a) providing a compound having the following structure:

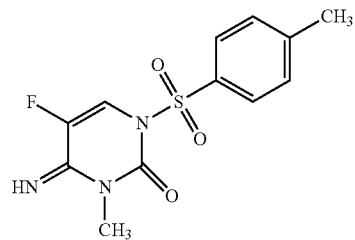

in an organic solvent; and b) filtering the precipitated solid from the solution of step a).

In some embodiments, the process wherein the organic solvent is toluene, isopropanol, tetrahydrofuran, methyl tert-butyl ether, cyclopentyl methyl ether, methyltetrahydrofuran and/or diethylcarbonate.

In some embodiments, the process wherein the organic solvent is toluene, isopropanol, tetrahydrofuran, or methyl tert-butyl ether.

In some embodiments, the process further comprising water mixed with the organic solvent.

In some embodiments, the process wherein the organic solvent is isopropanol.

In some embodiments, the process wherein the isopropanol-water mixture has a water activity of 0.1 or 0.3.

In some embodiments, the process comprising
a) providing the compound in toluene or tert-butyl ether; and
b) filtering the precipitated solid from the solution of step a),
wherein the crystalline polymorph is formed by suspension crystallization.

In some embodiments, the process comprising
a) providing the compound in toluene; and
b) filtering the precipitated solid from the solution of step a),
wherein the crystalline polymorph is formed by cooling crystallization.

In some embodiments, the process comprising
a) providing the compound in methyltetrahydrofuran and diethylcarbonate; and
b) filtering the precipitated solid from the solution of step a),
wherein the crystalline polymorph is formed by cooling crystallization.

In some embodiments, the process comprising
a) providing the compound in tetrahydrofuran; and
b) filtering the precipitated solid from the solution of step a),
wherein the crystalline polymorph is formed by evaporation crystallization.

In some embodiments, the process comprising
a) providing the compound in cyclopentyl methyl ether; and
b) filtering the precipitated solid from the solution of step a),
wherein the crystalline polymorph is formed by evaporation crystallization.

In some embodiments, the process wherein the solution is prepared at room temperature.

In some embodiments, the process wherein the solution is prepared at a temperature in the range of about 50° C. to about 60° C.

In some embodiments, the process wherein the solution is cooled to a temperature in the range of about 0° C. to about 10° C.

In some embodiments, the process wherein the solution in step a) is stirred at room temperature for 1-15 days before proceeding to step b).

In some embodiments, the process wherein the solution in step a) is stirred at room temperature for about 11 days before proceeding to step b).

In some embodiments, the process wherein the solution in step a) is stirred at room temperature for about 2 days before proceeding to step b).

In some embodiments, the process wherein the solution in step a) is stirred at room temperature for 0.5-24 hours before proceeding to step b).

In some embodiments, the process wherein the solution in step a) is stirred at room temperature for 2 hours before proceeding to step b).

In some embodiments, a process for preparing the crystalline polymorph form of Form II, comprising:

a) providing a solution of compound having the following structure:

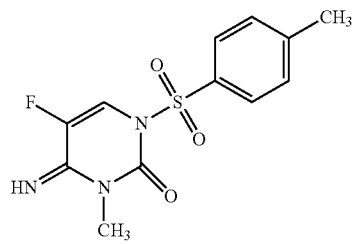

in an organic solvent; and b) filtering the precipitated solid from the solution of step a).

In some embodiments, the process wherein the organic solvent is methyl ethyl ketone or tetrahydrofuran.

In some embodiments, the process further comprising water mixed with the organic solvent.

In some embodiments, the process wherein the organic solvent is tetrahydrofuran.

In some embodiments, the process wherein the tetrahydrofuran-water mixture has a water activity of 0.1 or 0.3.

In some embodiments, the process comprising a) providing the compound in methyl ethyl ketone; and b) filtering the precipitated solid from the solution of step a), wherein the crystalline polymorph is formed by suspension crystallization.

In some embodiments, the process wherein the solution is prepared at room temperature.

In some embodiments, the process wherein the solution in step a) is stirred at room temperature for 1-15 days before proceeding to step b).

In some embodiments, the process wherein the solution in step a) is stirred at room temperature for about 11 days before proceeding to step b).

In some embodiments, the process wherein the solution in step a) is stirred at room temperature for about 2 days before proceeding to step b).

In some embodiments, the process wherein the solution in step a) is stirred at room temperature for 0.5-24 hours before proceeding to step b).

In some embodiments, the process wherein the solution in step a) is stirred at room temperature for 2 hours before proceeding to step b).

In some embodiments, a process for preparing the crystalline Hydrate form, comprising:

a) providing a solution of compound having the following structure:

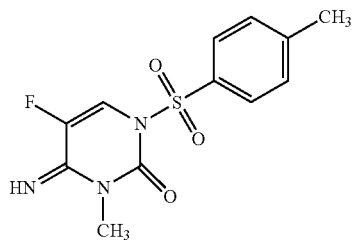

in an organic solvent; and b) filtering the precipitated solid from the solution of step a).

In some embodiments, the process wherein the organic solvent is acetonitrile, methanol, ethyl acetate, ethanol, acetone, tetrahydrofuran dichloromethane, methyltetrahydrofuran, and/or 1-propanol.

In some embodiments, the process wherein the organic solvent is acetonitrile, methanol, ethyl acetate, ethanol, acetone, tetrahydrofuran or dichloromethane.

In some embodiments, the process further comprising water mixed with the organic solvent.

In some embodiments, the process wherein water is mixed with methyltetrahydrofuran.

In some embodiments, the process wherein the organic solvent-water mixture is a 4:1 mixture of acetonitrile:water.

In some embodiments, the process comprising a) providing the compound in acetonitrile for at least 3 hours; and b) filtering the precipitated solid from the solution of step a), wherein the crystalline polymorph is formed by cooling crystallization.

In some embodiments, the process comprising a) providing the compound in methanol; and b) filtering the precipitated solid from the solution of step a), wherein the crystalline polymorph is formed by cooling crystallization.

In some embodiments, the process comprising a) providing the compound in ethanol for at least 3 days; and b) filtering the precipitated solid from the solution of step a), wherein the crystalline polymorph is formed by cooling crystallization.

In some embodiments, the process comprising a) providing the compound in ethyl acetate for at least 3 weeks; and b) filtering the precipitated solid from the solution of step a), wherein the crystalline polymorph is formed by cooling crystallization.

In some embodiments, the process comprising
a) providing the compound in methyltetrahydrofuran and methanol; and
b) filtering the precipitated solid from the solution of step a),
wherein the crystalline polymorph is formed by cooling crystallization.

In some embodiments, the process comprising
a) providing the compound in methyltetrahydrofuran and 1-propanol; and
b) filtering the precipitated solid from the solution of step a),
wherein the crystalline polymorph is formed by cooling crystallization.

In some embodiments, the process comprising
a) providing the compound in water mixed with methyltetrahydrofuran; and
b) filtering the precipitated solid from the solution of step a),
wherein the crystalline polymorph is formed by cooling crystallization.

In some embodiments, the process comprising
a) providing the compound in acetone; and
b) filtering the precipitated solid from the solution of step a),
wherein the crystalline polymorph is formed by evaporation crystallization.

In some embodiments, the process wherein the solution in step a) is stirred at about 25° C. for 1-15 days before proceeding to step b).

In some embodiments, the process wherein the solution in step a) is stirred at about 25° C. for 11 days before proceeding to step b).

In some embodiments, the process wherein the solution in step a) is stirred at about 25° C. for 2 days before proceeding to step b).

In some embodiments, the process wherein the solution in step a) is stirred at about 25° C. for 0.5-24 hours before proceeding to step b).

In some embodiments, the process wherein the solution in step a) is stirred at about 25° C. for 2 hours before proceeding to step b).

In some embodiments, the process comprising
a) providing the compound in dichloromethane; and
b) filtering the precipitated solid from the solution of step a),
wherein the crystalline polymorph is formed by evaporation crystallization.

In some embodiments, the process wherein the solution is prepared at about 60° C.

In some embodiments, the process wherein the solution is prepared at about 47° C.

In some embodiments, the process wherein the solution is prepared at about 52° C.

In some embodiments, wherein the solution is cooled to about 5° C.

In some embodiments, the process wherein the solution in step a) is stirred at about 25° C. for 16-20 hours before proceeding to step b).

In some embodiments, a process for preparing a mixture consisting of the crystalline polymorph form of Form I and the crystalline Hydrate form, comprising:

a) providing a solution of compound having the following structure:

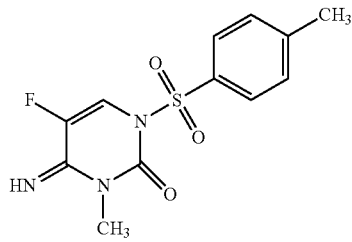

in an organic solvent; and
b) filtering the precipitated solid from the solution of step a).

In some embodiments, the process wherein the organic solvent is methyltetrahydrofuran and/or isopropanol.

In some embodiments, the process comprising
a) providing the compound in methyltetrahydrofuran and isopropanol; and
b) filtering the precipitated solid from the solution of step a),
wherein the crystalline polymorphs are formed by evaporation crystallization.

In some embodiments, the process wherein the solution is prepared at about 50° C.

In some embodiments, a process for preparing the crystalline solvate Form S5, comprising:

a) providing a solution of compound having the following structure:

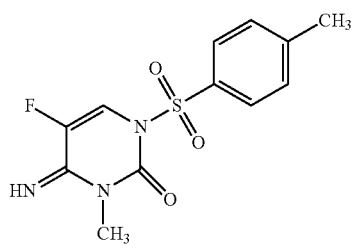 [SMILES: Cc1ccc(S(=O)(=O)n2cc(F)c(=N)n(C)c2=O)cc1]

in 1,4 dioxane; and
b) filtering the precipitated solid from the solution of step a).

In some embodiments, the process, wherein the solution is prepared at room temperature.

In some embodiments, the process wherein the solution in step a) is stirred at room temperature for 1-15 days before proceeding to step b).

In some embodiments, the process wherein the solution in step a) is stirred at room temperature for about 11 days before proceeding to step b).

In some embodiments, the process wherein the solution in step a) is stirred at about 25° C. for 2 days before proceeding to step b).

In some embodiments, the process wherein the solution in step a) is stirred at about 25° C. for 0.5-24 hours before proceeding to step b).

In some embodiments, the process wherein the solution in step a) is stirred at about 25° C. for 2 hours before proceeding to step b).

In some embodiments, a process for preparing the crystalline solvate Form S8, comprising:
a) providing a solution of compound having the following structure:

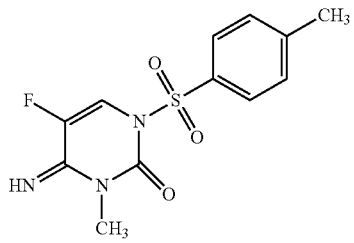

in tetrahydrofuran; and
b) filtering the precipitated solid from the solution of step a); and
c) concentrating the mother liquor from the filtering of step b) by evaporation.

In some embodiments, the process wherein the solution is prepared at about 30° C.

In some embodiments, the process wherein the solution in step a) is stirred at room temperature for 1-15 days before proceeding to step b).

In some embodiments, the process wherein the solution in step a) is stirred at room temperature for about 11 days before proceeding to step b).

In some embodiments, the process wherein the solution in step a) is stirred at about 25° C. for 2 days before proceeding to step b).

In some embodiments, the process wherein the solution in step a) is stirred at about 25° C. for 0.5-24 hours before proceeding to step b).

In some embodiments, the process wherein the solution in step a) is stirred at about 25° C. for 2 hours before proceeding to step b).

In some embodiments, the process wherein the solution in step a) is stirred at room temperature for 16-36 hours before proceeding to step b).

In some embodiments, the process wherein the solution in step a) is stirred at room temperature for about 24 hours before proceeding to step b).

In some embodiments, a process for preparing the crystalline solvate Form S1, comprising:
a) providing a solution of compound having the following structure:

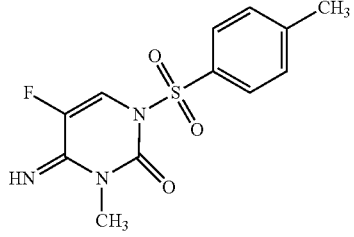 [SMILES: Cc1ccc(S(=O)(=O)n2cc(F)c(=N)n(C)c2=O)cc1]

in an ethyl acetate; and
b) filtering the precipitated solid from the solution of step a).

In some embodiments, the process wherein the solution is prepared at about 60° C.

In some embodiments, the process wherein the solution in step a) is stirred at room temperature for 1-15 days before proceeding to step b).

In some embodiments, the process wherein the solution in step a) is stirred at room temperature for about 11 days before proceeding to step b).

In some embodiments, the process wherein the solution in step a) is stirred at about 25° C. for 2 days before proceeding to step b).

In some embodiments, the process wherein the solution in step a) is stirred at about 25° C. for 0.5-24 hours before proceeding to step b).

In some embodiments, the process wherein the solution in step a) is stirred at about 25° C. for 2 hours before proceeding to step b).

In some embodiments, the process wherein the solution in step a) is stirred at about 25° C. for 16-20 hours before proceeding to step b).

In some embodiments, the process comprising
a) providing the compound in ethyl acetate; and
b) filtering the precipitated solid from the solution of step a),
wherein the crystalline polymorph is formed by cooling crystallization.

In one embodiment, a process of manufacturing a fungicidal composition which comprises obtaining the crystalline form of the present invention, and combining the crystalline with an excipient so as to thereby manufacture the fungicidal composition.

In one embodiment, a process of manufacturing a fungicidal composition which comprises obtaining the crystalline form of the present invention, and combining the crystalline form with an adjuvant so as to thereby manufacture the fungicidal composition.

In one embodiment, a process of manufacturing a fungicidal composition which comprises obtaining the mixture of the present invention, and combining the mixture with an excipient so as to thereby manufacture the fungicidal composition.

In one embodiment, a process of manufacturing a fungicidal composition which comprises obtaining the mixture of the present invention, and combining the mixture with an adjuvant so as to thereby manufacture the fungicidal composition.

In some embodiments of the above process, comprising further combining a fungicide with the crystalline form or mixture and the excipient or adjuvant.

The present invention also provides a fungicidal composition comprising a solution of the compound having the structure:

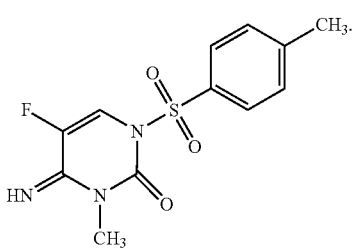

The present invention also provides a fungicidal composition comprising a solution of the crystalline form of the present invention or of the mixture of the present invention.

In some embodiments, the fungicidal composition further comprises at least one excipient.

In some embodiments, the fungicidal composition further comprises at least one excipient for preparation of a tank mix.

The present invention also provides a method for the control of fungal attack on a plant, the method comprising:

i) obtaining a solution of the compound having the structure:

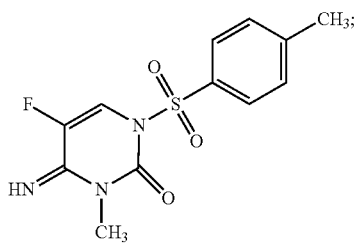

and ii) applying the solution to a locus of the fungus, to a locus in which the infestation is to be prevented, and/or to the plant, so as to thereby control fungal attack on the plant.

The present invention also provides a method for the control of fungal attack on a plant, the method comprising:

i) obtaining a solution of the crystalline form or of the mixture of the present invention; and ii) applying the solution to a locus of the fungus, to a locus in which the infestation is to be prevented, and/or to the plant, so as to thereby control fungal attack on the plant.

In some embodiments, the method wherein the mixture is a tank mix.

In some embodiments, the method wherein the tank mix further comprises at least one excipient.

In some embodiments, the disclosed crystalline form and/or mixture of disclosed crystalline forms with at least one other pesticidal compound and/or the composition comprising the crystalline form of the present invention (including a mixture with at least one other pesticidal compound) is applied to the roots, seeds or foliage of plants for the control of various fungi, without damaging the commercial value of the plants.

In some embodiments, the disclosed crystalline form and/or mixture of disclosed crystalline form with at least one other pesticidal compound is may be applied to the roots, seeds or foliage of plants for the control of various fungi, without damaging the commercial value of the plants.

In some embodiments, there is provided a crystalline form of the compound (a Polymorph Form I or II, a Hydrate or a Solvate Form S1, S5 or S8), which is present as a material comprising at least about 50% or more by weight of the polymorph, hydrate, solvate or mixture thereof based on the total amount of compound. In some aspects, the crystalline form is present as a material comprising at least about 60% by weight of the polymorph, hydrate or solvate based on the total amount of compound. In some aspects, the crystalline form is present as a material comprising at least about 70% by weight of the polymorph, hydrate or solvate based on the total amount of compound. In some aspects, the crystalline form is present as a material comprising at least about 80% by weight of the polymorph, hydrate or solvate based on the total amount of compound. In some aspects, the crystalline form is present as a material comprising at least about 90% by weight of the polymorph, hydrate or solvate based on the total amount of compound. In some aspects, the crystalline form is present as a material comprising at least about 95% by weight of the polymorph, hydrate or solvate based on the total amount of compound. In some aspects, the crystalline form is present as a material comprising at least about 98% by weight of the polymorph, hydrate or solvate based on the total amount of compound. In some aspects, the crystalline form is present as a material comprising at least about 99% by weight of the polymorph, hydrate or solvate based on the total amount of compound.

In some embodiments, there is a provided crystalline polymorph Form I or II, which is present as a material that is substantially free of amorphous compound and substantially free of hydrates or solvates of the compound.

The formulations or compositions comprising or consisting essentially the disclosed crystalline forms are prepared according to procedures which are conventional in the agricultural chemical art. See, for example, Foy, C. L. and Pritchard, D. W. (1996) Pesticide Formulation and Adjuvant Technology. CRC Press.

Concentrated formulations of the disclosed crystalline form can be dispersed in water, or another liquid, for application, or formulations can be dust-like or granular, which can then be applied without further treatment. The formulations are prepared according to procedures which are conventional in the agricultural chemical art, but which are novel and important because of the presence therein of a crystalline form. Concentrated formulations of the disclosed crystalline form can be dispersed in water, or another liquid, for application, or formulations can be dust-like or granular, can be dilute before application.

The concentration of the disclosed crystalline form and/or mixture of disclosed crystalline form with at least one other pesticidal compound in formulation is usually from about 0.5% to about 90% by weight, more preferably about 25% to about 75% by weight, based on the total weight of the formulation.

The formulations that are applied most often are aqueous suspensions or emulsions. Either such water-soluble, water-suspendable, or emulsifiable formulations are solids, usually known as wettable powders, or liquids, usually known as emulsifiable concentrates, aqueous suspensions, or suspension concentrates. The present disclosure contemplates all vehicles by which the synergistic compositions can be formulated for delivery and used as a fungicide.

As will be readily appreciated, any material to which the disclosed compositions can be added may be used, provided they yield the desired utility without significant interference with the activity of these synergistic compositions as antifungal agents.

Wettable powders, which may be compacted to form water-dispersible granules, comprise an intimate mixture of the synergistic composition, a carrier and agriculturally acceptable surfactants. The concentration of the disclosed composition in the wettable powder is usually from about 10% to about 90% by weight, more preferably about 25% to about 75% by weight, based on the total weight of the formulation. In the preparation of wettable powder formulations, the synergistic composition can be compounded with any of the finely divided solids.

The disclosed compositions may optionally include combinations that can comprise at least 1% by weight of one or more of the compositions with another pesticidal compound. Such additional pesticidal compounds may be fungicides, insecticides, nematocides, miticides, arthropodicides, bactericides or combinations thereof that are compatible with the synergistic compositions of the present disclosure in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from 1:100 to 100:1.

Solids exist in either amorphous or crystalline forms. In the case of crystalline forms, molecules are positioned in 3-dimensional lattice sites.

When a compound recrystallizes from a solution or slurry, it may crystallize with different spatial lattice arrangements, a property referred to as "polymorphism," With the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. Solvates are crystalline solid adducts containing either stoichiometric or nonstoichiometric amounts of a solvent incorporated within the crystal structure. If the incorporated solvent is water, the solvates are also commonly known as hydrates. Solvate or hydrate are also commonly known as "pseudopolymorph".

New polymorphic, hydrate or solvate forms can provide various advantages, including improved physical characteristics such as stability or solubility. The polymorphs disclosed herein are purer and are more efficacious.

As used herein, the term "mixture" or "combination" refers, but is not limited, to a combination in any physical form, e.g., blend, solution, alloy, or the like.

As used herein, the term "composition" includes a mixture or mixtures of the crystalline form of the compound of the present invention with another component, including at least one additional fungicide.

As used herein, the term "tank mix" means one or more of the components of the mixture or composition of the present invention and/or one or more of the excipients which are added are mixed in a spray tank at the time of spray application or prior to spray application.

As used herein, the term "excipient" refers to any chemical which has no pesticidal activity, such as surfactant(s), solvent(s), or adjuvant(s). One or more excipients can be added to any mixture or composition disclosed herein.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of."

The term "about" herein specifically includes ±10% from the indicated values in the range. In addition, the endpoints of all ranges directed to the same component or property herein are inclusive of the endpoints, are independently combinable, and include all intermediate points and ranges.

In yet another embodiment, the product of any of the disclosed processes can be isolated from the reaction mixture by any conventional techniques well-known in the art. Such isolation techniques can include, without limitation, one or more of the following: concentration, extraction, precipitation, cooling, filtration, crystallization, and centrifugation, followed by drying.

In yet another embodiment, the product of any of the disclosed processes can be optionally purified by any conventional techniques well-known in the art. Such purification techniques may include, without limitation, one or more of the following: precipitation, crystallization, slurrying, washing in a suitable solvent, filtration through a packed-bed column, dissolution in an appropriate solvent, and re-precipitation by addition of a second solvent in which the compound is insoluble, or any combination thereof.

While the present subject matter has been shown and described with reference to preferred embodiments thereof, it will be understood by those skilled in the art that many alternatives, modifications and variations may be made thereto without departing from the spirit and scope thereof. Accordingly, it is intended to embrace all such alternatives, modifications, and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

The following examples illustrate the practice of the present subject matter in some of its embodiments, but should not be construed as limiting the scope of the present subject matter. Other embodiments will be apparent to one skilled in the art from consideration of the specification and examples. It is intended that the specification, including the examples, is considered exemplary only, without limiting the scope and spirit of the present subject matter.

Experimental Details

XRPD: Stoe Stadi P with Mythen1K detector; Cu-K$\alpha$1 radiation; 40 kV and 40 mA tube power; curved Ge monochromator; 0.02° 2θ step size, 12 s step time, 1.5-50.5° 2θ scanning range; detector mode: step scan; 1° 2θ detector step. The sample (20-40 mg) was placed either between two acetate foils (dry samples) or between two Kapton foils (wet samples) and clamped in a Stoe transmission sample holder; the sample holder was rotated during the measurement.

XRPD: Bruker D8 Advance; Cu-K$\alpha$ radiation; standard measurement conditions: Bragg-Brentano reflection geometry; 40 kV and 40 mA tube power; LynxEye detector; 0.02° 2θ step size, 37 s step time, 2.5-50.5° 2θ scanning range (about 10 min measurement time); rotating the sample holder during the measurement. The sample was spread on a silicon single-crystal substrate without cavity and flattened to fit to the 0.5 mm depth of the sample holder.

All sample preparation and measurement was done in an ambient air atmosphere; the wet samples were analyzed immediately after preparation.

FT-Raman Spectroscopy: Bruker Multi-RAM with OPUS 6.5 software; Nd:YAG 1064-nm excitation, Ge detector, 3500-50 cm-1 range; typical measurement conditions: 300 mW nominal laser power, 64 scans, 2 cm-1 resolution; samples pressed into the cavity of aluminum sample holders
TG-FTIR: Netzsch Thermo-Microbalance TG 209 with Bruker FT-IR Spectrometer Vector 22; aluminum crucible (with microhole); N2 atmosphere; 10° C./min heating rate, from 25 to 300° C.

DSC: TA Instruments DSC Q2000; hermetically closed gold crucible; N2 atmosphere; 10° C./min heating rate, from 20 to 190° C. The melting point is understood as the peak onset.

Solvents: For all experiments, Fluka, Merck or ABCR analytical grade solvents were used. For experiments under dry conditions and preparing water-organic solvent mixtures with accurate water activity the organic solvents were previously dried over molecular sieves (4 Å) for a few days.

The composition of the solvent mixtures with water and organic solvent for a certain water activity at a given temperature was taken from J. Gmehling, U. Onken, Vapor-Liquid-Equilibrium Data Collection, in: D. Behrens, R. Eckermann, Chemistry Data Series, Dechema, Frankfurt, 1977. The composition of solvent mixtures is understood in volume ratios, unless specified otherwise.

Example 1. Form I

All of the examples below resulted in Form I.
Form I was prepared by suspension crystallization.
1) About 100 mg of 5-fluoro-4-imino-3-methyl-1-tosyl-3,4-dihydropyrimidin-2(1H)-one was suspended in 1.0 ml of 2-PrOH previously dried over 4 Å molecular sieves and the suspension was stirred for 11 d at RT and filtered through a 0.2-µm PTFE centrifuge filter and analyzed without drying, or dried in dry $N_2$ stream at RT for 1 h.
2) About 100 mg of 5-fluoro-4-imino-3-methyl-1-tosyl-3,4-dihydropyrimidin-2(1H)-one was suspended in 1.0 ml of tert-butyl methyl ether (TBME) previously dried over 4 Å molecular sieves and the suspension was stirred for 11 d at RT, filtered through a 0.2-µm PTFE centrifuge filter and analyzed without drying.
3) About 100 mg of 5-fluoro-4-imino-3-methyl-1-tosyl-3,4-dihydropyrimidin-2(1H)-one was suspended in 1.0 ml of toluene previously dried over 4 Å molecular sieves and the suspension was stirred for 11 d at RT, filtered through a 0.2-µm PTFE centrifuge filter and analyzed without drying.
4) About 1800 gr of 5-fluoro-4-imino-3-methyl-1-tosyl-3,4-dihydropyrimidin-2(1H)-one was suspended in 16000 gr of toluene and the suspension was stirred for two hours at 30° C. The solid was filtered in centrifuge filter, washed with 1 liter of toluene and dried at 65° C.
5) About 100 mg of 5-fluoro-4-imino-3-methyl-1-tosyl-3,4-dihydropyrimidin-2(1H)-one was suspended in 2.0 ml of 2-PrOH/water=99.7/0.3 (v/v) at RT (aw=0.1) or 2.0 ml of 2-PrOH/water=97.5/2.5 (v/v) at RT (aw=0.1) and the suspension was stirred for 3 d at RT; over the weekend it turned into an apparently more diluted suspension; it was seeded with an unstable solvate form, Form I and Form II and stirred for further 2 d; then it was filtered through a 0.2-µm PTFE centrifuge filter and the solid was analyzed without drying or the solid was allowed to dry under ambient conditions for 5 d.

Form I was also prepared by cooling crystallization.
1) About 100 mg of 5-fluoro-4-imino-3-methyl-1-tosyl-3,4-dihydropyrimidin-2(1H)-one was dissolved in 4.0 ml of toluene (previously dried over 4 Å molecular sieves) at 60° C.; the solution was filtered hot through a 0.45-µm PTFE filter; the clear solution was cooled at a constant rate down to 25° C. within 4 h and magnetically stirred for further 16 h; the opalizing solution was stored at 5° C. for 1 d and then at −25° C. for 3 d without stirring; the solid was filtered through a 0.22-µm PTFE centrifuge filter and analyzed wet without any drying or were dried in dry $N_2$ stream at RT for 1 h.
2) About 7 gr of 5-fluoro-4-imino-3-methyl-1-tosyl-3,4-dihydropyrimidin-2(1H)-one was dissolved in 95 gr of toluene; the solution was washed with water, mixed for one hour at 50° C., and then cooled to 10° C.; the solid was filtered in a centrifuge filter, dried in a vacuum oven, and analyzed.
3) About 6 gr of 5-fluoro-4-imino-3-methyl-1-tosyl-3,4-dihydropyrimidin-2(1H)-one was dissolved in 14 gr of MeTHF and 19 gr of diethylcarbonate; the solution was heated to 55° C. and then cooled to 0° C.; the solid was filtered in a centrifuge filter and analyzed without drying.

Form I was also prepared by evaporation crystallization.
1) About 150 mg of 5-fluoro-4-imino-3-methyl-1-tosyl-3,4-dihydropyrimidin-2(1H)-one was dissolved in 2.0 ml of THF at 30° C.; the solution was filtered through a 0.45-µm PTFE filter; the clear solution was let evaporate by a gentle $N_2$ stream at RT; when about ¾ of the solvent evaporated, it turned into a suspension; it was stirred for additional 1 d and became thicker as the vial was left open for ambient air through the needle; the solid was filtered through a 0.22-µm PTFE centrifuge filter and analyzed without drying or were allowed to dry under ambient conditions for 2 d.
2) About 6.7 gr of 5-fluoro-4-imino-3-methyl-1-tosyl-3,4-dihydropyrimidin-2(1H)-one was dissolved in 30 gr of cyclopentyl methyl ether (CPME); the solution was mixed, partially evaporated at 60° C. (185 mbar), and then cooled; the solid was filtered in a centrifuge filter and analyzed without drying.
3) About 6 gr of 5-fluoro-4-imino-3-methyl-1-tosyl-3,4-dihydropyrimidin-2(1H)-one was dissolved in 54 gr of CPME; the solution was washed with water at 50° C.; CPME was evaporated from the solution to dryness; the solid was analyzed.

Form I was also prepared by dehydration of the Hydrate.
1) Measuring by DSC in an open pan, the water of crystallization evaporates in the temperature range of 20-100° C. Then a sharp endothermic event due to melting follows in the thermogram at 159° C. (FIG. 10). The melting point coincides with that of Form I; therefore the dehydration of the hemihydrate results in anhydrous Form I.

Example 2. Form II

The example below resulted in Form II.
Form II was prepared by suspension crystallization. About 120 mg of 5-fluoro-4-imino-3-methyl-1-tosyl-3,4-dihydropyrimidin-2(1H)-one was suspended in 0.8 ml of methyl ethyl ketone (MEK) previously dried over 4 Å molecular sieves and the suspension was stirred for 11 d at room temperature and filtered through a 0.2-µm PTFE centrifuge filter. The solid was allowed to dry under ambient conditions for 1 d.

Example 3. Hydrate

All of the examples below resulted in Hydrate.
Hydrate was prepared by suspension crystallization.
1) About 100 mg of 5-fluoro-4-imino-3-methyl-1-tosyl-3,4-dihydropyrimidin-2(1H)-one was suspended in 2.0 ml of THF/water=78.7/21.3 (v/v) at RT (aw=0.9); it turned into a clear solution and additional 85 mg of solid was added; the suspension was stirred for 3 d at RT; over the weekend it turned into an apparently more diluted suspension; it was seeded with an unstable solvate form, Form I and Form II and stirred for further 2 d; then it was filtered through a 0.2-µm PTFE centrifuge filter and the solid was analyzed without drying or allowed to dry under ambient conditions for 5 d.
2) About 90 mg of 5-fluoro-4-imino-3-methyl-1-tosyl-3,4-dihydropyrimidin-2(1H)-one was suspended in 0.5 ml of THF/water-96.4/3.6 (v/v) at RT (aw=0.7); it almost dissolved but became slightly denser within a few minutes; after 1 d of stirring it was seeded with Hydrate, Form I and Form II, and stirred for further 2 d; then it was filtered through a 0.2-µm PTFE centrifuge filter and the solid was analyzed without drying.

3) About 100 mg of 5-fluoro-4-imino-3-methyl-1-tosyl-3,4-dihydropyrimidin-2(1H)-one was suspended in 2.0 ml of 2-PrOH/water=94.7/5.3 (v/v) at RT (aw=0.5); it became a clear solution and additional 100 mg of solid also dissolved in the solution; another 130 mg of solid was added; the suspension became rather think but still could be stirred; it was stirred for 3 d at RT; over the weekend it turned into an apparently much more diluted suspension; it was seeded with Hydrate, Form I and Form II and stirred for further 2 d; then it was filtered through a 0.2-μm PTFE centrifuge filter and the solid was allowed to dry under ambient conditions for 5 d.

Hydrate was also prepared by cooling crystallization.

1) About 100 mg of 5-fluoro-4-imino-3-methyl-1-tosyl-3,4-dihydropyrimidin-2(1H)-one was dissolved in 2.0 ml of MeOH (previously dried over 4 Å molecular sieves) at 60° C.; the solution was filtered hot through a 0.45-μm PTFE filter; the clear solution was cooled at a constant rate down to 25° C. within 4 h and magnetically stirred for further 16 h; the solid was filtered through a 0.22-μm PTFE centrifuge filter and analyzed without drying or were allowed to dry under ambient conditions for 3 d and analyzed.

2) About 100 mg of 5-fluoro-4-imino-3-methyl-1-tosyl-3,4-dihydropyrimidin-2(1H)-one was dissolved in 4.0 ml of EtOH (previously dried over 4 Å molecular sieves) at 60° C.; the solution was filtered hot through a 0.45-μm PTFE filter; the clear solution was cooled at a constant rate down to 25° C. within 4 h and magnetically stirred for further 16 h; the solid was filtered through a 0.22-μm PTFE centrifuge filter to form an unstable solvate which was allowed to dry under ambient conditions for 3 d.

3) About 120 mg of 5-fluoro-4-imino-3-methyl-1-tosyl-3,4-dihydropyrimidin-2(1H)-one was dissolved in 1.0 ml of MeCN (previously dried over 4 Å molecular sieves) at 60° C.; the solution was filtered hot through a 0.45-μm PTFE filter; the clear solution was cooled at a constant rate down to 25° C. within 4 h and magnetically stirred for further 16 h to form an unstable solvate which was allowed to dry under ambient conditions for 3 d.

4) About 120 mg of 5-fluoro-4-imino-3-methyl-1-tosyl-3,4-dihydropyrimidin-2(1H)-one was dissolved in 1.0 ml of EtOAc (previously dried over 4 Å molecular sieves) at 60° C.; the solution was filtered hot through a 0.45-μm PTFE filter; the clear solution was cooled at a constant rate down to 25° C. within 4 h and magnetically stirred for further 16 h; the solid was allowed to dry under ambient conditions for 3 d; about four weeks later the solid was dried at 40° C. in a stream of dry $N_2$ for 20 h.

5) About 7.6 gr of 5-fluoro-4-imino-3-methyl-1-tosyl-3,4-dihydropyrimidin-2(1H)-one was dissolved in 170 gr of MeTHF and 65 gr of water for 30 minutes at 60° C.; the solution was cooled slowly; the solid was filtered through a centrifuge filter and analyzed without drying.

6) About 4 gr of 5-fluoro-4-imino-3-methyl-1-tosyl-3,4-dihydropyrimidin-2(1H)-one was dissolved in 2θ gr of MeTHF and 32 gr of MeOH; the solution was heated to 47° C. and cooled slowly to 5° C.; the solid was filtered through a centrifuge filter, dried in a vacuum oven at 55° C., and analyzed.

7) About 2 gr of 5-fluoro-4-imino-3-methyl-1-tosyl-3,4-dihydropyrimidin-2(1H)-one was dissolved in 10 gr of MeTHF and 15 gr n-PrOH; the solution was heated to 52° C. and cooled slowly to 5° C.; the solid was filtered through a centrifuge filter, dried in a vacuum oven at 55° C., and analyzed.

Hydrate was also prepared by evaporation crystallization.

1) About 150 mg of 5-fluoro-4-imino-3-methyl-1-tosyl-3,4-dihydropyrimidin-2(1H)-one was dissolved in 2.0 ml of DCM at 30° C.; the solution was filtered through a 0.45-μm PTFE filter; the clear solution was let evaporate by a gentle $N_2$ stream at RT; the evaporation was stopped when about 0.2 ml solvent was left; the next day the solution seemed to evaporate to dryness; the samples was taken out from the vial after one additional day.

2) About 150 mg of 5-fluoro-4-imino-3-methyl-1-tosyl-3,4-dihydropyrimidin-2(1H)-one was dissolved in 2.0 ml of acetone at 30° C.; the solution was filtered through a 0.45-μm PTFE filter; the clear solution was allowed to evaporate at RT through a needle in the septum; the next day the evaporation was accelerated by a gentle $N_2$ stream; when about half of the solvent had evaporated, the crystals appeared on the wall of the vial were suspended in the solution and the obtained suspension was stirred at RT for additional 1 d; the solid was filtered through a 0.22-μm PTFE centrifuge filter to form an unstable solvate which was allowed to dry under ambient conditions for 2 d.

Crude Hydrate product is purified by crystallization/precipitation from a warmed solution (40° C.) of the solid in solution of acetonitrile by addition of water in the ratio of 2:1. To 1100 gr crude compound were added 3500 gr acetonitrile. The mixture was heated to 60° C. and 1000 gr of acetonitrile were added however the mixture was not clear. The mixture copied to 40° C. and 7530 gr of water were added. The mixture was cooled to 15° C., filtered and dried in vacuum oven 55° C., 10 mbar.

Example 4. Form I and Hydrate

The example below resulted in a mixture of Form I and Hydrate.

A mixture of Form I and Hydrate was prepared by evaporation crystallization. About 6.7 gr of 5-fluoro-4-imino-3-methyl-1-tosyl-3,4-dihydropyrimidin-2(1H)-one was dissolved in 75 gr of MeTHF; the solution was washed with water; 25 gr of MeTHF was evaporated from the solution; 75 gr of 2-PrOH was added and the solution was heated to 50° C.; the solution was cooled; the solid was filtered in a centrifuge filter and analyzed.

Example 5. Solvate S5

All of the examples below resulted in Solvate S5.

Solvate S5 was prepared by suspension crystallization. About 120 mg of 5-fluoro-4-imino-3-methyl-1-tosyl-3,4-dihydropyrimidin-2(1H)-one was suspended in 0.8 ml of 1,4-dioxane previously dried over 4 Å molecular sieves and the suspension was stirred for 11 d at RT, filtered through a 0.2-μm PTFE centrifuge filter and analyzed without drying or allowed to dry under ambient conditions for 1 d.

Solvate S5 was prepared by evaporation crystallization. The mother liquor of the above suspension crystallization procedure was allowed to evaporate to dryness at RT; the solid was dried in dry $N_2$ stream at RT for 1 d or dried at 40° C. in a stream of dry $N_2$ for 20 h and analyzed.

Example 6. Solvate S8

The example below resulted in Solvate S8.

Solvate S8 was prepared by evaporation crystallization. About 150 mg of 5-fluoro-4-imino-3-methyl-1-tosyl-3,4-dihydropyrimidin-2(1H)-one was dissolved in 2.0 ml of THF at 30° C.; the solution was filtered through a 0.45-μm PTFE filter; the clear solution was let evaporate by a gentle $N_2$ stream at RT; when about ¾ of the solvent evaporated, it turned into a suspension; it was stirred for additional 1 d and became thicker as the vial was left open for ambient air through the needle; the solid was filtered through a 0.22-µm PTFE centrifuge filter and analyzed without drying or were allowed to dry under ambient conditions for 2 d. The mother liquor of the above evaporation crystallization procedure was allowed to evaporate to dryness at RT or was dried at 40° C. in a stream of dry $N_2$ for 20 h to provide Solvate S8.

Example 7. Solvate S1

All of the examples below resulted in Solvate S1.

Solvate S1 was prepared by suspension crystallization. About 100 mg of 5-fluoro-4-imino-3-methyl-1-tosyl-3,4-dihydropyrimidin-2(1H)-one was suspended in 1.0 ml of EtOAc previously dried over 4 Å molecular sieves and the suspension was stirred for 11 d at RT, filtered through a 0.2-µm PTFE centrifuge filter and analyzed without drying.

Solvate S1 was also prepared by cooling crystallization. About 120 mg of -fluoro-4-imino-3-methyl-1-tosyl-3,4-dihydropyrimidin-2(1H)-one was dissolved in 1.0 ml of EtOAc (previously dried over 4 Å molecular sieves) at 60° C.; the solution was filtered hot through a 0.45-µm PTFE filter; the clear solution was cooled at a constant rate down to 25° C. within 4 h and magnetically stirred for further 16 h; the solid was analyzed wet without any drying, or dry under ambient conditions for 3 d, or dried at 40° C. in a stream of dry $N_2$ for 2θ h.

Example 8. Critical Water Activity

The critical water activity between the Hydrate and anhydrous Forms I and II was attempted to be determined at room temperature in 2-PrOH/water and THF/water mixtures. The starting material was suspended with the solvent mixture first and after a few days of slurrying the suspension was seeded with the hemihydrate and anhydrous Form I and Form II. After two additional days of stirring at RT, the solid was separated from the liquid by centrifuge filtering. The experimental conditions and the obtained results are shown in Table 1.

TABLE 1

| Solvent | $a_w$ [a] | Seeded with [b] | Result (XRPD) [c] |
|---|---|---|---|
| 2PrOH/water = 99.3/0.7 | 0.1 | HH + Form I + Form II | Form I |
| 2PrOH/water = 97.5/2.5 | 0.3 | HH + Form I + Form II | Form I |
| 2PrOH/water = 94.7/5.3 | 0.5 | HH + Form I + Form II | HH' |
| THF/water = 96.4/3.6 | 0.7 | HH + Form I + Form II | Form II |
| THF/water = 79.7/21.3 | 0.9 | HH + Form I + Form II | HH" |

[a] the water activity is taken from J. Gmehling, U. Onken, Vapor-Liquid-Equilibrium Data Collection
[b] the starting material (PP539-P1) was seeded after 3 d of slurrying with samples PP539-P17A, -P9A and -P3A
[c] the solid part of the slurries was analyzed wet immediately after centrifuge filtering The results show that at a water activity of 0.3 and below the anhydrous Form I is the thermodynamically most stable among the three forms suspended. At a water activity of 0.5 and 0.9 the hemihydrate form seems to be more stable. However, Form II was found to be more stable in the suspension at a water activity of 0.7. This latter finding, namely that a hydrate form is more stable than an anhydrous form both below and after a certain water activity at the same temperature, contradicts the lows of thermodynamics; therefore it is assumed to be untrue.

In order to clarify the root cause of the surprising results regarding the critical water activities, three further experiments were performed. The slurries at water activities of 0.5 and 0.7 were repeated using freshly prepared solvent mixtures and the suspension equilibration at a water activity of 0.7 was also performed in 2-PrOH/water mixture. The formation of thick suspension in 2-PrOH/water mixtures was experienced again; the initially obtained thick suspension turned into a well-stirred slurry upon one day of stirring. Then it was seeded with the three forms and the solid was isolated after additional two days of stirring. The experimental conditions and the obtained results are shown in Table 2.

TABLE 2

| Solvent | $a_w$ [a] | Seeded with [b] | Result (XRPD) [c] |
|---|---|---|---|
| 2PrOH/water = 94.7/5.3 | 0.5 | HH + Form I + Form II | HH" + some Form II |
| THF/water = 96.4/3.6 | 0.7 | HH + Form I + Form II | HH' |
| 2PrOH/water = 89.6/10.4 | 0.7 | HH + Form I + Form II | HH" + traces of Form II |

[a] the water activity is taken from J. Gmehling, U. Onken, Vapor-Liquid-Equilibrium Data Collection
[b] the starting material (PP539-P1) was seeded after 1 d of slurrying with samples PP539-P28A, -P25A and -P27A
[c] the solid part of the slurries was analyzed wet immediately after centrifuge filtering The hemihydrate proved to be more stable than the two anhydrous forms in all the suspensions; however, in 2-PrOH/water mixtures the conversion was not complete and a small fraction of Form II was detected. This is very likely due to the poor solubility in the solvent mixture. The hemihydrate again exhibited slightly different patterns as obtained from various experiments. The diffraction pattern slightly varies from sample to sample; its actual shape does not seem to have a direct correlation with the water activity the sample was equilibrated with. The ultimate finding is that the hemihydrate is more stable than the two anhydrous forms (Form I and Form II) at a water activity of 0.5 and higher at RT.

Example 9. Relative Stability of Forms I and II

Based on the DSC results, Form II has a lower melting point and higher melting enthalpy than Form I (156° C. and 112 J/g vs. 159° C. and 110 J/g). This implies that the two forms are enantiotropically related: Form II being the thermodynamically more stable form at lower temperatures and Form I the more stable one at higher temperatures. However, the difference in the melting enthalpies is rather small and not necessarily reliable (only one measurement was performed with both samples). Therefore, it is also possible that the two forms are monotropically related and Form I is the more stable form at all temperatures below melting.

The relative thermodynamic stability of the polymorphs was determined by slurry experiments at RT and 5° C. Form I proved to be more stable at water activities of 0.1 and 0.3 and such result is already evidence that it is thermodynamically more stable than Form II at RT. The stability was further investigated at 5° C. and in addition, another experiment was performed at MEK at RT. MEK was chosen as suspending media because that was the only solvent where Form II was formed when slurrying the starting material. The solubility is rather high in MEK; therefore the conversion into the more stable form should be rather quick at both temperatures. The experiment at 5° C. in TBME was actually carried out only as a control. The experimental conditions applied and the results obtained are shown in Table 3.

TABLE 3

| Solvent [a] | Temperature | Seeded with [b] | Result (XRPD) [c] |
|---|---|---|---|
| MEK (dry) | 22° C. | Form I + Form II | Form I + Form II |
| MEK (dry) | 5° C. | Form I + Form II | Form S9 + Form I |
| TBME (dry) | 5° C. | Form I + Form II | Form I |

[a] the solvents were dried over molecular sieves prior to use
[b] the starting material (PP539-P1) was seeded after 4 h of slurrying with samples PP539-P25A and -P27A
[c] the solid part of the slurries was analyzed wet immediately after centrifuge filtering The results show that Form I was found to be unequivocally more stable than Form II only in TBME at 5° C. The ultimate finding of these competitive slurry experiments is that Form I and Form II are either monotropically related, Form I being the thermodynamically more stable form; or they are enantiotropically related Form I being the high temperature form which is more stable at 5° C. and above.

Discussion

The crystalline forms of the present application provide stable forms that are more easily formulated for agricultural use. The crystalline solvate forms of the present invention provide an advantage in organic reaction procedure. The different solvates provide flexibility in organic solvents which can be used in particular at the separation stage. The obtained solvate forms are precipitated and can be easily filtered and washed.

Also, the crystalline hydrate form of the present invention provides an advantage in reaction where the separating stage can be conducted in aqueous phase. The hydrate form is easily precipitated, filtered and washed in presence of water.

The crystalline form I of the present application provides an advantage in granulation procedure. It can be easily milled and used for preparing suspensions liquid and solid formulation.

Suspension crystallization, cooling crystallization and/or evaporation crystallization revealed that 5-fluoro-4-imino-3-methyl-1-tosyl-3,4-dihydropyrimidin-2(1H)-one either forms solvates with EtOAc (Form S1), 1,4-dioxane (Form S5), and THF (Form S8).

It was also found that 5-fluoro-4-imino-3-methyl-1-tosyl-3,4-dihydropyrimidin-2(1H)-one does not form thermodynamically stable solvates with toluene, 2-PrOH and TBME at RT. In these suspensions the compound formed the anhydrous polymorph Form I.

It was found that 5-fluoro-4-imino-3-methyl-1-tosyl-3,4-dihydropyrimidin-2(1H)-one does not form thermodynamically stable solvates with MEK at RT. In these suspensions the compound formed the anhydrous polymorph Form II.

5-Fluoro-4-imino-3-methyl-1-tosyl-3,4-dihydropyrimidin-2(1H)-one forms a hydrate with water.

Form I is purer than the Hydrate form. Form I is thermodynamically more stable than polymorph Form II at 5° C. and above, it is thermodynamically more stable than the hydrate form at a water activity of 0.3 or less at room temperature and it is non-hygroscopic and thereby shows a high kinetic stability against hydration also at higher relative humidity in the solid state (where the hydrate would be thermodynamically more stable).

What is claimed is:

1. A crystalline form of the compound having the following structure:

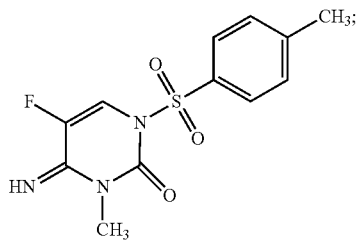 [SMILES: Cc1ccc(S(=O)(=O)n2cc(F)c(=N)n(C)c2=O)cc1]

wherein the crystalline form is:
a) Form I having an X-ray powder diffraction pattern with characteristic peaks at 2-theta angles of 14.05, 17.51, 18.75 and 21.63;
b) Form II having an X-ray powder diffraction pattern with characteristic peaks at 2-theta angles of 9.20, 11.88, 22.33 and 22.59;
c) a Hydrate Form having an X-ray powder diffraction pattern with characteristic peaks at 2-theta angles of 5.34, 7.48, 10.68 and 16.05;
d) Solvate Form S1 having an X-ray powder diffraction pattern with characteristic peaks at 2-theta angles of 5.34, 7.48, 10.68 and 21.83;
e) Solvate Form S5 having an X-ray powder diffraction pattern with characteristic peaks at 2-theta angles of 5.42, 7.50, 10.82 and 16.91; or
f) Solvate Form S8 having an X-ray powder diffraction pattern with characteristic peaks at 2-theta angles of 4.7, 5.00, 9.66 and 23.97.

2. The crystalline form of claim 1, wherein the crystalline form is Solvate Form S1, Solvate Form S5 or Solvate Form S8 and wherein the solvate contains 1,4-dioxane, tetrahydrofuran, or ethyl acetate.

3. The crystalline form of claim 1, wherein the crystalline form is Form I having a powder X-ray diffraction pattern in accordance with the pattern of FIG. 1.

4. The crystalline form of claim 3, characterized by:
a. a Differential Scanning calorimetry (DSC) curve showing an endothermic peak with a peak temperature of about 160° C.;
b. a Differential Scanning calorimetry (DSC) curve showing an endothermic peak with an onset temperature of about 159° C.;
c. a Differential Scanning calorimetry (DSC) curve showing an endothermic peak with a melting enthalpy of about 110 J/g; and/or
d. a TG-FTIR thermogram showing decomposition begins at a temperature greater than 210° C.

5. The crystalline form of claim 1, wherein the crystalline form is Form II having a powder X-ray diffraction pattern in accordance with the pattern of FIG. 4.

6. The crystalline form of claim 5, characterized by:
a. a Differential Scanning calorimetry (DSC) curve showing an endothermic peak with a peak temperature of about 157° C.;
b. a Differential Scanning calorimetry (DSC) curve showing an endothermic peak with an onset temperature of about 156° C.;
c. a Differential Scanning calorimetry (DSC) curve showing an endothermic peak with a melting enthalpy of about 112 J/g; and/or d. a TG-FTIR thermogram showing decomposition begins at a temperature greater than 210° C.

7. The crystalline form of claim 1, wherein the crystalline Hydrate Form has a powder X-ray diffraction pattern in accordance with the pattern of FIG. 7.

8. The crystalline form of claim 7, characterized by:
a. a Differential Scanning calorimetry (DSC) curve showing an endothermic peak with a peak temperature of about 139.5° C., wherein the DSC is measured in a sealed pan;
b. a Differential Scanning calorimetry (DSC) curve showing an endothermic peak with an onset temperature of about 139° C., wherein the DSC is measured in a sealed pan;
c. a Differential Scanning calorimetry (DSC) curve showing an endothermic peak with a melting enthalpy of about 115 J/g, wherein the DSC is measured in a sealed pan;
d. a Differential Scanning calorimetry (DSC) curve showing an endothermic peak with a peak temperature of about 160° C., wherein the DSC is measured in an open pan;
e. a Differential Scanning calorimetry (DSC) curve showing an endothermic peak with an onset temperature of about 159° C., wherein the DSC is measured in an open pan;
f. a Differential Scanning calorimetry (DSC) curve showing an endothermic peak with a melting enthalpy of about 98 J/g, wherein the DSC is measured in an open pan; and/or
g. a TG-FTIR thermogram showing decomposition begins at a temperature greater than 190° C.

9. The crystalline form of claim 2, wherein:
a. Solvate Form S5 has a powder X-ray diffraction pattern in accordance with the pattern of FIG. 11;
b. Solvate Form S8 has a powder X-ray diffraction pattern in accordance with the pattern of FIG. 13; or
c. Solvate Form S1 has a powder X-ray diffraction pattern in accordance with the pattern of FIG. 15.

10. The crystalline form of claim 9, characterized by:
a. a TG-FTIR thermogram showing decomposition begins at a temperature greater than 180° C. or
b. a TG-FTIR thermogram showing decomposition begins at a temperature greater than 200° C.

11. A mixture of crystalline forms of the compound having the following structure:

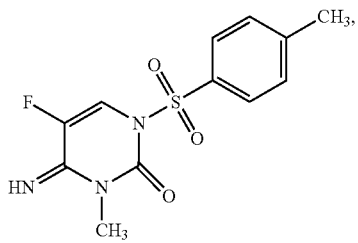

which is a mixture of one or more crystalline forms of claim 1.

12. A fungicidal composition comprising:
a. the crystalline form of claim 1; or
b. the crystalline form of claim 1, and one or more fungicidal carriers.

13. The composition of claim 12, further comprising at least one additional fungicide.

14. A method for the control of fungal attack on roots and/or seeds and/or a plant, the method comprising:
a. i) obtaining the crystalline form of claim 1 or a solution of the crystalline form of claim 1; and
    ii) applying the crystalline form or the solution to a locus of the fungus, to a locus in which the infestation is to be controlled, and/or to the roots and/or seeds and/or plant, so as to thereby control fungal attack on the roots and/or seeds and/or plant; or
b. applying the crystalline form of claim 1, to a locus in which the infestation is to be controlled, and/or to the roots and/or seeds and/or plant, so as to thereby control fungal attack on the roots and/or seeds and/or plant; or
c. applying a synergistic fungicidal mixture to a locus of the fungus, to a locus in which the infestation is to be controlled, and/or to the roots and/or seeds and/or plant, the mixture comprising:
    i) a fungicidally effective amount of the crystalline form of claim 1; and
    ii) at least one additional fungicide,
so as to thereby control fungal attack on the roots and/or seeds and/or plant.

15. A method (a) for the control of fungal attack on a plant, the method comprising:
    i) obtaining a composition of claim 12; and
    ii) applying the composition to a locus of the fungus, to a locus in which the infestation is to be controlled, and/or to the plant, so as to thereby control fungal attack on the plant; or
(b) for the control of fungal attack on a plant and/or roots and/or seeds, the method comprising:
    i) obtaining a composition of claim 12; and
    ii) applying the composition to the roots, seeds or foliage of plants for the control of various fungi, without damaging the commercial value of the plants.

16. A process for preparing the crystalline anhydrous polymorph form of claim 3, comprising:
    i) providing a compound having the following structure:

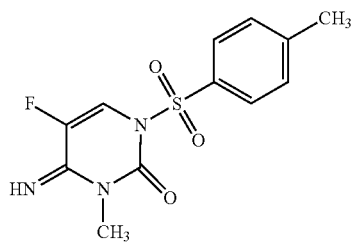

in an organic solvent; and
    ii) filtering the precipitated solid from the solution of step i).

17. A process for preparing the crystalline anhydrous polymorph form of claim 5, comprising:

i) providing a solution of compound having the following structure:

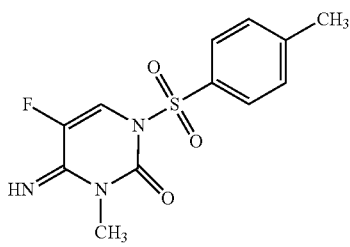

in an organic solvent; and ii) filtering the precipitated solid from the solution of step i).

18. A process for preparing the crystalline hydrate form of claim 7, comprising:

i) providing a solution of compound having the following structure:

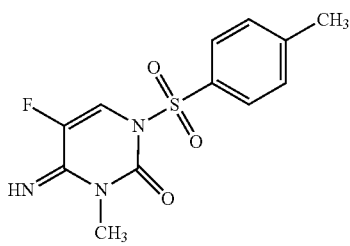

in an organic solvent; and ii) filtering the precipitated solid from the solution of step i).

19. A process for preparing the crystalline solvate form of claim 9, comprising:

a. i) providing a solution of compound having the following structure:

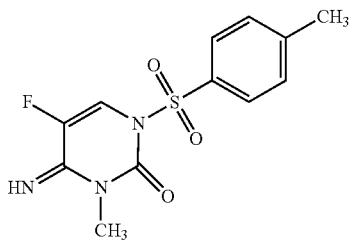

in 1,4 dioxane; and ii) filtering the precipitated solid from the solution of step i);

b. i) providing a solution of compound having the following structure:

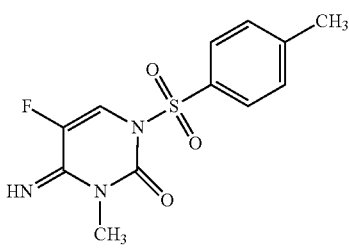

in tetrahydrofuran; and ii) filtering the precipitated solid from the solution of step i); and iii) concentrating the mother liquor from the filtering of step ii) by evaporation; or c. i) providing a solution of compound having the following structure:

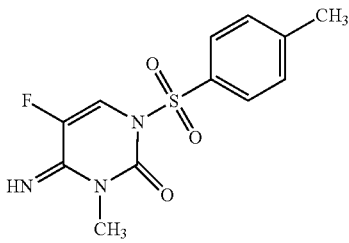 [SMILES: Cc1ccc(S(=O)(=O)n2cc(F)c(=N)n(C)c2=O)cc1]

in an ethyl acetate; and ii) filtering the precipitated solid from the solution of step i).

20. A process for preparing the crystalline form of claim 1, wherein:

a. the crystalline form is prepared by cooling crystallization of the compound having the following structure:

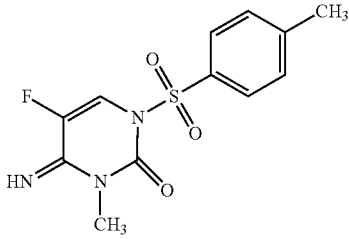 [SMILES: Cc1ccc(S(=O)(=O)n2cc(F)c(=N)n(C)c2=O)cc1]

in a suitable solvent;

b. the crystalline form is prepared by evaporation crystallization of the compound having the following structure:

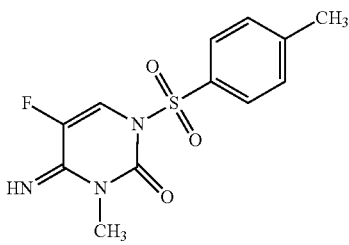

in a suitable solvent; or c. the crystalline form is prepared by suspension crystallization of the compound having the following structure:

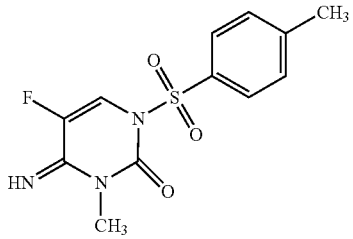 [SMILES: Cc1ccc(S(=O)(=O)n2cc(F)c(=N)n(C)c2=O)cc1]

in a suitable solvent.

21. The crystalline form of the compound of claim 1, wherein the crystalline form is:
   a) Form I having an X-ray powder diffraction pattern with characteristic peaks at 2-theta angles of 9.08, 10.98, 14.05, 17.51, 18.75, 21.63, 23.33, 24.70, 24.83, 25.37, 26.51 and 29.23;
   b) Form II having an X-ray powder diffraction pattern with characteristic peaks at 2-theta angles of 7.98, 9.20, 9.96, 11.88, 15.99, 18.49, 21.23, 22.33, 22.59 and 26.73;
   c) a Hydrate Form having an X-ray powder diffraction pattern with characteristic peaks at 2-theta angles of 5.34, 7.48, 10.68, 16.05, 21.79, 22.99, 23.19, 24.95, 26.95 and 27.63;
   d) Solvate Form S1 having an X-ray powder diffraction pattern with characteristic peaks at 2-theta angles of 5.34, 7.48, 10.10, 10.68, 12.90, 16.07, 21.83, 23.09, 24.91 and 26.93;
   e) Solvate Form S5 having an X-ray powder diffraction pattern with characteristic peaks at 2-theta angles of 5.42, 7.50, 10.06, 10.82, 12.80, 16.91, 21.55, 23.13, 24.83, 26.81 and 27.77; or
   f) Solvate Form S8 having an X-ray powder diffraction pattern with characteristic peaks at 2-theta angles of 4.7, 5.00, 5.38, 6.26, 9.66, 15.93, 21.05, 23.97 and 24.69.

22. The crystalline form of claim 1, wherein the crystalline form is Form I having an X-ray powder diffraction pattern with characteristic peaks at 2-theta angles of 14.05, 17.51, 18.75 and 21.63; or Form II having an X-ray powder diffraction pattern with characteristic peaks at 2-theta angles of 9.20, 11.88, 22.33 and 22.59.

23. A mixture of crystalline forms of the compound having the following structure:

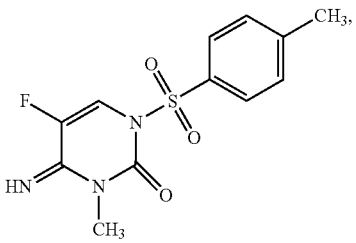

which is a mixture of one or more of the crystalline forms of claim 22 and any one or more of the following crystalline forms:
   a) a Hydrate Form having an X-ray powder diffraction pattern with characteristic peaks at 2-theta angles of 5.34, 7.48, 10.68 and 16.05;
   b) Solvate Form S1 having an X-ray powder diffraction pattern with characteristic peaks at 2-theta angles of 5.34, 7.48, 10.68 and 21.83;
   c) Solvate Form S5 having an X-ray powder diffraction pattern with characteristic peaks at 2-theta angles of 5.42, 7.50, 10.82 and 16.91; and
   d) Solvate Form S8 having an X-ray powder diffraction pattern with characteristic peaks at 2-theta angles of 4.7, 5.00, 9.66 and 23.97.

24. A method for the control of fungal attack on roots and/or seeds and/or a plant, the method comprising:
   a. i) obtaining the crystalline form of claim 22 or a solution of the crystalline form of claim 22; and
      ii) applying the crystalline form or the solution to a locus of the fungus, to a locus in which the infestation is to be controlled, and/or to the roots and/or seeds and/or plant, so as to thereby control fungal attack on the roots and/or seeds and/or plant; or
   b. applying the crystalline form of claim 22, to a locus in which the infestation is to be controlled, and/or to the roots and/or seeds and/or plant, so as to thereby control fungal attack on the roots and/or seeds and/or plant; or
   c. applying a synergistic fungicidal mixture to a locus of the fungus, to a locus in which the infestation is to be controlled, and/or to the roots and/or seeds and/or plant, the mixture comprising:
      i) a fungicidally effective amount of the crystalline form of claim 22; and
      ii) at least one additional fungicide,
   so as to thereby control fungal attack on the roots and/or seeds and/or plant.

25. A fungicidal composition comprising:
   a. the crystalline form of claim 22; or
   b. the crystalline form of claim 22, and one or more fungicidal carriers.

26. A method (a) for the control of fungal attack on a plant, the method comprising:
   i) obtaining a composition of claim 25; and
   ii) applying the composition to a locus of the fungus, to a locus in which the infestation is to be controlled, and/or to the plant, so as to thereby control fungal attack on the plant; or
   (b) for the control of fungal attack on a plant and/or roots and/or seeds, the method comprising:
   i) obtaining a composition of claim 25; and
   ii) applying the composition to the roots, seeds or foliage of plants for the control of various fungi, without damaging the commercial value of the plants.

27. A process for preparing the crystalline form of claim 22, wherein:
   a. the crystalline form is prepared by cooling crystallization of the compound having the following structure:

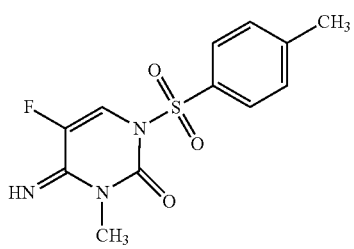

in a suitable solvent;
b. the crystalline form is prepared by evaporation crystallization of the compound having the following structure:

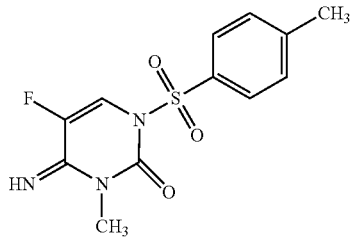

in a suitable solvent; or
c. the crystalline form is prepared by suspension crystallization of the compound having the following structure:

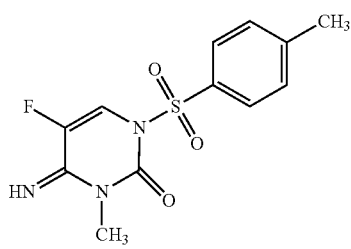 [SMILES: Cc1ccc(S(=O)(=O)n2cc(F)c(=N)n(C)c2=O)cc1]

in a suitable solvent.

28. The crystalline form of claim 1, wherein the crystalline form is a Hydrate Form having an X-ray powder diffraction pattern with characteristic peaks at 2-theta angles of 5.34, 7.48, 10.68, 16.05, 21.79, 22.99, 23.19, 24.95, 26.95 and 27.63.

29. A mixture of crystalline forms of the compound having the following structure:

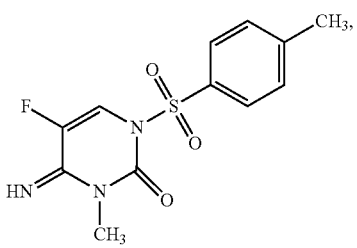

which is a mixture of the crystalline form of claim 28 and any one or more of the following crystalline forms:
a) Form I having an X-ray powder diffraction pattern with characteristic peaks at 2-theta angles of 14.05, 17.51, 18.75 and 21.63;
b) Form II having an X-ray powder diffraction pattern with characteristic peaks at 2-theta angles of 9.20, 11.88, 22.33 and 22.59;
c) Solvate Form S1 having an X-ray powder diffraction pattern with characteristic peaks at 2-theta angles of 5.34, 7.48, 10.68 and 21.83;
d) Solvate Form S5 having an X-ray powder diffraction pattern with characteristic peaks at 2-theta angles of 5.42, 7.50, 10.82 and 16.91; and
e) Solvate Form S8 having an X-ray powder diffraction pattern with characteristic peaks at 2-theta angles of 4.7, 5.00, 9.66 and 23.97.

30. A method for the control of fungal attack on roots and/or seeds and/or a plant, the method comprising:
a. i) obtaining the crystalline form of claim 28 or a solution of the crystalline form of claim 28; and
  ii) applying the crystalline form or the solution to a locus of the fungus, to a locus in which the infestation is to be controlled, and/or to the roots and/or seeds and/or plant, so as to thereby control fungal attack on the roots and/or seeds and/or plant; or
b. applying the crystalline form of claim 28, to a locus in which the infestation is to be controlled, and/or to the roots and/or seeds and/or plant, so as to thereby control fungal attack on the roots and/or seeds and/or plant; or
c. applying a synergistic fungicidal mixture to a locus of the fungus, to a locus in which the infestation is to be controlled, and/or to the roots and/or seeds and/or plant, the mixture comprising:
  i) a fungicidally effective amount of the crystalline form of claim 28; and
  ii) at least one additional fungicide,
so as to thereby control fungal attack on the roots and/or seeds and/or plant.

31. A fungicidal composition comprising:
a. the crystalline form of claim 28; or
b. the crystalline form of claim 28, and one or more fungicidal carriers.

32. A method (a) for the control of fungal attack on a plant, the method comprising:
i) obtaining a composition of claim 31; and
ii) applying the composition to a locus of the fungus, to a locus in which the infestation is to be controlled, and/or to the plant, so as to thereby control fungal attack on the plant; or
(b) for the control of fungal attack on a plant and/or roots and/or seeds, the method comprising:
i) obtaining a composition of claim 31; and
ii) applying the composition to the roots, seeds or foliage of plants for the control of various fungi, without damaging the commercial value of the plants.

33. A process for preparing the crystalline form of claim 28, wherein:
a. the crystalline form is prepared by cooling crystallization of the compound having the following structure:

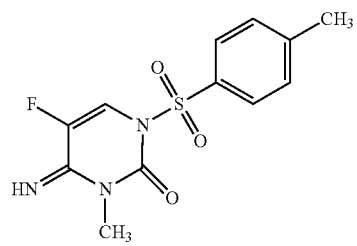

in a suitable solvent;
b. the crystalline form is prepared by evaporation crystallization of the compound having the following structure:

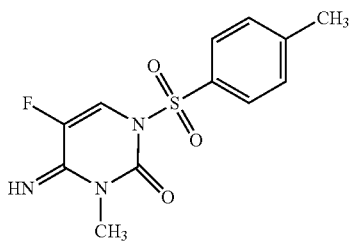

in a suitable solvent; or c. the crystalline form is prepared by suspension crystallization of the compound having the following structure:

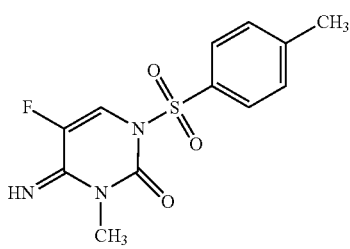

in a suitable solvent.

34. The crystalline form of claim 1, wherein the crystalline form is Solvate Form S1 having an X-ray powder diffraction pattern with characteristic peaks at 2-theta angles of 5.34, 7.48, 10.68 and 21.83; Solvate Form S5 having an X-ray powder diffraction pattern with characteristic peaks at 2-theta angles of 5.42, 7.50, 10.82 and 16.91; or Solvate Form S8 having an X-ray powder diffraction pattern with characteristic peaks at 2-theta angles of 4.7, 5.00, 9.66 and 23.97.

35. A mixture of crystalline forms of the compound having the following structure:

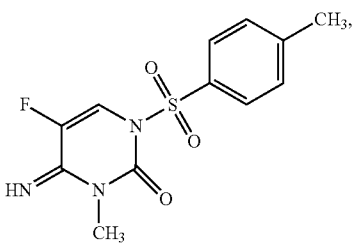

which is a mixture of any one or more of the crystalline forms of claim 34 and any one or more of the following crystalline forms:

a) Form I having an X-ray powder diffraction pattern with characteristic peaks at 2-theta angles of 14.05, 17.51, 18.75 and 21.63;

b) Form II having an X-ray powder diffraction pattern with characteristic peaks at 2-theta angles of 9.20, 11.88, 22.33 and 22.59; and c) a Hydrate Form having an X-ray powder diffraction pattern with characteristic peaks at 2-theta angles of 5.34, 7.48, 10.68 and 16.05.

36. A method for the control of fungal attack on roots and/or seeds and/or a plant, the method comprising:

a. i) obtaining the crystalline form of claim 34 or a solution of the crystalline form of claim 34; and ii) applying the crystalline form or the solution to a locus of the fungus, to a locus in which the infestation is to be controlled, and/or to the roots and/or seeds and/or plant, so as to thereby control fungal attack on the roots and/or seeds and/or plant; or b. applying the crystalline form of claim 34, to a locus in which the infestation is to be controlled, and/or to the roots and/or seeds and/or plant, so as to thereby control fungal attack on the roots and/or seeds and/or plant; or c. applying a synergistic fungicidal mixture to a locus of the fungus, to a locus in which the infestation is to be controlled, and/or to the roots and/or seeds and/or plant, the mixture comprising:

i) a fungicidally effective amount of the crystalline form of claim 34; and ii) at least one additional fungicide, so as to thereby control fungal attack on the roots and/or seeds and/or plant.

37. A fungicidal composition comprising:

a. the crystalline form of claim 34; or b. the crystalline form of claim 34, and one or more fungicidal carriers.

38. A method (a) for the control of fungal attack on a plant, the method comprising:

i) obtaining a composition of claim 37; and ii) applying the composition to a locus of the fungus, to a locus in which the infestation is to be controlled, and/or to the plant, so as to thereby control fungal attack on the plant; or (b) for the control of fungal attack on a plant and/or roots and/or seeds, the method comprising:

i) obtaining a composition of claim 37; and ii) applying the composition to the roots, seeds or foliage of plants for the control of various fungi, without damaging the commercial value of the plants.

39. A process for preparing the crystalline form of claim 34, wherein:

a. the crystalline form is prepared by cooling crystallization of the compound having the following structure:

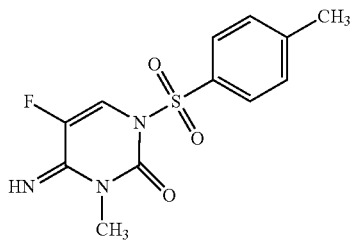 [SMILES: Cc1ccc(S(=O)(=O)n2cc(F)c(=N)n(C)c2=O)cc1]

in a suitable solvent;

b. the crystalline form is prepared by evaporation crystallization of the compound having the following structure:

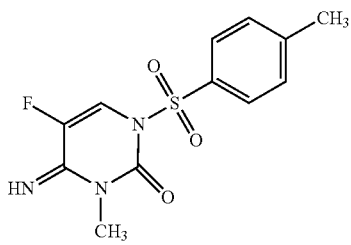
in a suitable solvent; or
c. the crystalline form is prepared by suspension crystallization of the compound having the following structure:
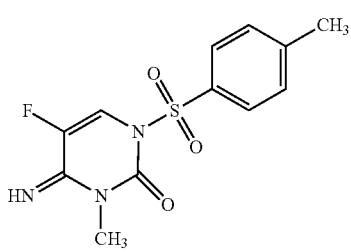
in a suitable solvent.
* * * * *